US007807437B2

(12) United States Patent
Schildgen et al.

(10) Patent No.: US 7,807,437 B2
(45) Date of Patent: Oct. 5, 2010

(54) VARIANTS OF HEPATITIS B VIRUS RESISTANT AGAINST SOME NUCLEOSIDE ANALOGUES, BUT SENSITIVE TO OTHERS, AND USES THEREOF

(75) Inventors: Oliver Schildgen, Cologne (DE); Martin Vogel, Bonn (DE); Bertfried Matz, Bonn (DE); Juergen Rockstroh, Cologne (DE); Rolf Kaiser, Bonn (DE); Martin Daeumer, Bonn (DE); Martin Helm, Nuernberg (DE); Lutwin Weitner, Hamburg (DE); Carl Knud Schewe, Hamburg (DE); Wolfram Gerlich, Marburg (DE)

(73) Assignees: Rheinishche Friedrich-Wilhelms-Universitaet Bonn, Bonn (DE); Universitaet Zu Koeln, Cologne (DE); Justus-Liebig-Universitaet Gissen, Giessen (DE)

( * ) Notice: Subject to any disclaimer, the term of this patent is extended or adjusted under 35 U.S.C. 154(b) by 0 days.

(21) Appl. No.: 11/375,580

(22) Filed: Mar. 15, 2006

(65) Prior Publication Data
US 2007/0042356 A1    Feb. 22, 2007

Related U.S. Application Data

(60) Provisional application No. 60/661,483, filed on Mar. 15, 2005.

(30) Foreign Application Priority Data

Mar. 15, 2005 (EP) .................................. 05102014

(51) Int. Cl.
C12N 7/00 (2006.01)
(52) U.S. Cl. .................................................. 435/235.1
(58) Field of Classification Search ........................ None
See application file for complete search history.

(56) References Cited

U.S. PATENT DOCUMENTS

| 6,555,311 | B1 | 4/2003 | Locarnini |
| 2003/0124096 | A1 | 7/2003 | Locarnini |
| 2006/0165725 | A1 | 7/2006 | Bozdayi |
| 2006/0234212 | A1 | 10/2006 | Bozdayi |
| 2007/0042356 | A1 | 2/2007 | Schildgen |

FOREIGN PATENT DOCUMENTS

| WO | WO 94/26904 | 11/1994 |
| WO | 97/40193 | 10/1997 |
| WO | WO 98/21317 | 5/1998 |
| WO | WO 00/58477 | 10/2000 |
| WO | WO 00/61758 | 10/2000 |
| WO | 03/066841 | 8/2003 |
| WO | WO 03/087351 | 10/2003 |
| WO | WO 2004/031224 | 4/2004 |

OTHER PUBLICATIONS

Angus et al., Resistance to Adefovir Dipivoxil Therapy Associated With the Selection of a Novel Mutation in the HBV Polymerase, Gastroenterology, 2003, 125:292-297.*
Bartholomeusz et al., Comparisons of the HBV and HIV polymerase, and antiviral resistance mutations, Antiviral Therapy, 2004, 9:149-160.*
Tacke et al., Basal Core Promoter and Precore Mutations in the Hepatitis B Virus Genome Enhance Replication Efficacy of Lamivudine-Resistant Mutants, Journal of Virology, 2004, 78(16):8524-8535.*
GenBank Accession No. AB367435.*
GenBank Accession No. AB367434.*
GenBank Accession No. AB367429.*
European Search Report dated Nov. 30, 2005, issued connection with corresponding EP 05102014.7
Alexopoulou A et al, J General Virology (1996), vol. 3, pp. 173-181, "Whole genome analysis of hepatitis B virus from four cases of fulminant hepatitis: genetic variability and its potential role in disease pathogenicity" Table 3.
Aye et al, "Hepatitis B Virus Polymerase Mutations During Famciclovir Therapy in Patients Following Liver Transplantation", Hepatology vol. 24, No. 4, Pt.2, Abstract 633, Sep. 1996.
Aye et al, "Hepatitis B Virus polymerase mutations during antiviral therapy in a patient following liver transplantation", Journal of Hepatology, 1997; 26: 1148-1153.
Bartholomeusz et al, "Mutations in the hepatitis B virus polymerase gene that are associated with resistance to famciclovir and lamivudine",1997, International Antiviral News , vol. 5, No. 8, pp. 123-124.
Bartholomew, "Hepatitis-B-virus resistance to lamivudine given for recurrent infection after orthotopic liver transplantation", (Lancet 349: Jan. 20-22, 1997).
Bowyer S et al, J General Virology (1997), vol. 78, pp. 1719-1729, "A unique segment of the hepatitis B virus group A genotype identified in isolates from South Africa" Figure 5.
Bozdayi et al "A new mutation pattern (YMDD->YSDD) in the YMDD motif of HBV-DNA polymerase gene in chronic B hepatitis infection resistant to lamivudine" Journal of Hepatology, 2001, 34(1):162-162. Meeting Abstract.
Carman et al, "Vaccine-induced escape mutant . . .", The Lancet, vol. 336, 1990 (8711) pp. 325-329.

(Continued)

Primary Examiner—Zachariah Lucas
Assistant Examiner—Nicole Kinsey White
(74) Attorney, Agent, or Firm—Nixon & Vanderhye P.C.

(57) ABSTRACT

The present invention relates generally to the field of Hepatitis B variants exhibiting a reduced sensitivity to nucleoside analogues both in vivo and in vitro. More in particular, reverse transcriptase mutant rt I233V is provided. Present invention provides assays and methods for detecting such variant, which assays are useful in monitoring anti-viral therapeutic regimes and adjusting patient therapy. A diagnostic kit for detecting the presence of an HBV variant in a biological sample has also been described. Finally, the use of a pharmaceutical composition to cure a subject suffering from a HBV infection, which HBV is resistant to lamuvidine and/or adefovir has been provided, which pharmaceutical composition comprises the nucleoside analogue tenofovir.

18 Claims, 9 Drawing Sheets

OTHER PUBLICATIONS

Figure 1:
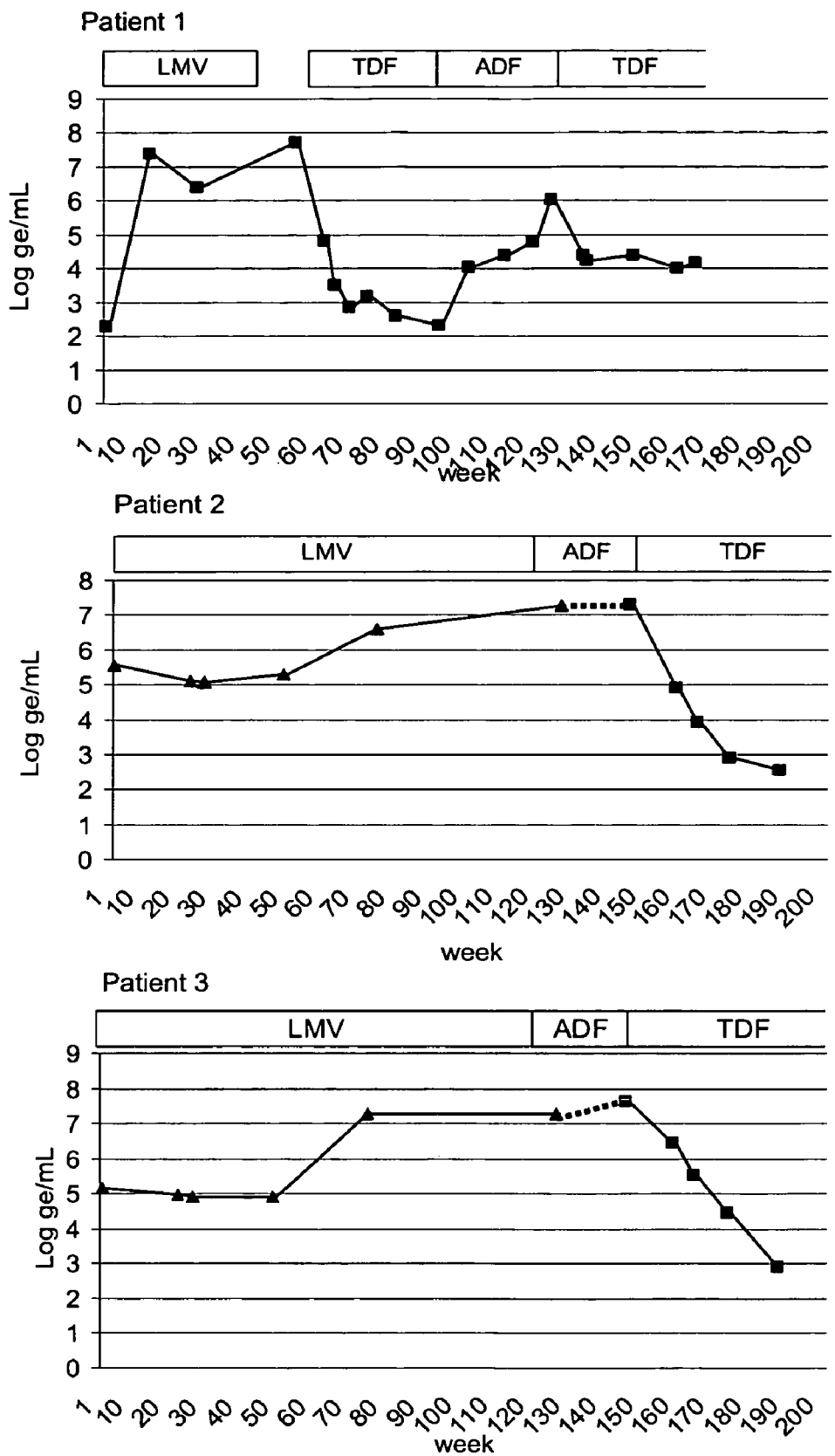

Carman, "The clinical significance of surface antigen variants . . . ", Journal of Viral Hepatitis, 1997. 4 (Suppl. 1) 11-20.

Chenault, "Patterns of nucleotide sequence variation among cauliflower mosaic virus isolates", (Biochimie 76:3-8, 1994).

de Man et al, "The sequential occurrence of viral mutations in a liver transplant recipient re-infected with hepatitis B: hepatitis B immune globuline escape, famciclovir non-respnse, followed by lamivudine resistance resulting in graft loss", Journal of Hepatology, 1998; 29: 669-675.

Delaney et al, "Phenylpropenamide Derivatives AT-61 and AT-130 Inhibit Replication of Wild-Type and Lamivudine-Resistant Strains of Hepatitis B Virus In Vitro", Antimicrobial Agents and Chemotherapy, Sep. 2002, vol. 46, No. 9, pp. 3057-3060.

Delaney et al, "Resistance of hepatitis B virus to antiviral drugs: current aspects and directions for future investigation", Antiviral Chemistry & Chemotherapy 12:1-35 (2001).

Fischer et al, "Generation of Duck Hepatitis B Virus Polymerase Mutants through Site-Directed Mutagenesis Which Demonstrate Resistance to Lamivudine [(-)-β-L-2',3'-Dideoxy-3'-Thiacytidine] In Vitro", Antimicrobial Agents & Chemotherapy 40: 1957-1960, Aug. 1996.

Fujii et al, "Gly[145] to Arg Substitution in HBs Antigen of . . . ", Biochemical and Biophysical Research Communications, vol. 184, No. 3, May 15, 1992, pp. 1152-1157.

Gaillard et al, "Kinetic Analysis of Wild-Type and YMDD Mutant Hepatitis B Virus Polymerases and Effects of Deoxyribonucleotide Concentrations on Polymerase Activity", Antimicrobial Agents and Chemotherapy, Apr. 2002, vol. 46, No. 4, pp. 1005-1013.

Gerner et al, "Hepatitis B Virus Core Promoter Mutations in Children with Multiple Anti-HBe/HBeAg Reactivations Result in Enhanced Promoter Activity", Journal of Medical Virology 59:415-423 (1999).

Han et al, "YMDD Motif Mutants in Hepatitis B Virus Polymerase during Lamivudine Therapy", Korean J. Genetics 24(2):219-226 (Jun. 2002).

Ho et al,, "A Family Cluster of an Immune Escape Variant of Hepatitis B Virus Infecting a Mother and Her Two Fully Immunized Children", Clinical and Diagnostic Laboratory Immunology, 1995, vol. 2, No. 6, pp. 760-762.

Horikita M et al, J Medical Virology (1994), vol. 44(1), pp. 96-103, "Differences in the entire nucleotide sequence between hepatitis B virus genomes from carriers positive for antibody to hepatitis B e antigen with and without active disease" Table IV.

Ling ("Selection of mutations in hepatitis B virus polymerase during therapy of transplant recipients with lamivudine" Hepatology 24(3): 711-713, Sep. 1996).

Ni F et al, Research in Virology (1995), vol. 146(6), pp. 397-407, "A new immune escape mutant of hepatitis B virus with an Asp to Ala substitution in aa144 of the envelope major protein" Figure 3.

Niesters et al, "Identification of a new variant in the YMDD motif of the hepatitis B virus polymerase gene selected during lamivudine therapy", J. Med. Microbiol., vol. 51 (2002), 695-699.

Norder , "Molecular basis of hepatitis B virus serotype variations within the four major subtypes", (Virology 198: 489-503, 1994).

Norder et al, "Molecular basis of hepatitis B virus serotype variations within the four major subtypes", Journal of General Virology 1992, vol. 73, pp. 3141-3145.

Norder H et al, J General Virology (1992), vol. 73(5), pp. 1201-1208, "Comparison of the amino acid sequences of nine different scrotypes of hepatitis B surface antigen and genomic classification of the corresponding hepatitis B strains" Figure 3.

Norder H et al, J General Virology (1993), vol. 74, pp. 1341-1348, "Genetic relatedness of hepatitis B viral strains of diverse geographical origin and natural variations in the primary structure of the surface antigen" Figure 2.

Okamoto F et al, J. General Virology (1988), vol 69, pp. 2575-2583, "Typing hepatitis B virsu by homology in nucleotide sequence: comparison of surface antigen subtypes" Figure 1.

Ono Y et al, Nucleic Acids Research(1983), vol. 11(6), pp. 1747-1757, "The complete nucleotide sequence of the cloned hepatitis B virus DNA; subtype *adr* and *adw*" Figure 2 and 3.

Pasek M et al, Nature(1979), vol. 282, pp. 575-579, "Hepatitis B virus genes and their expression in *E. coli*" Figure 2.

Perrillo et al, "Adefovir Dipivoxil Added to Ongoing Lamivudine in Chronic Hepatitis B with YMDD Mutant Hepatitis B Virus", Gastroenterology 2004; 126:81-90.

Poch et al, "Identification of four conserved motifs among the RNA-dependent polymerase encoding elements" EMBO Journal 8: 3867-3874, 1989.

Ren H et al, "Expression of 12 antibody escape mutants of hepatitis B virus surface antigen gene in mammalian cell by using an Epstein-Barr based vector", Chung Hua I Hseuh Tsa Chih 1995 75(7) pp. 396-398 (PubMed English Abstract PMID 7553156).

Figure 5:
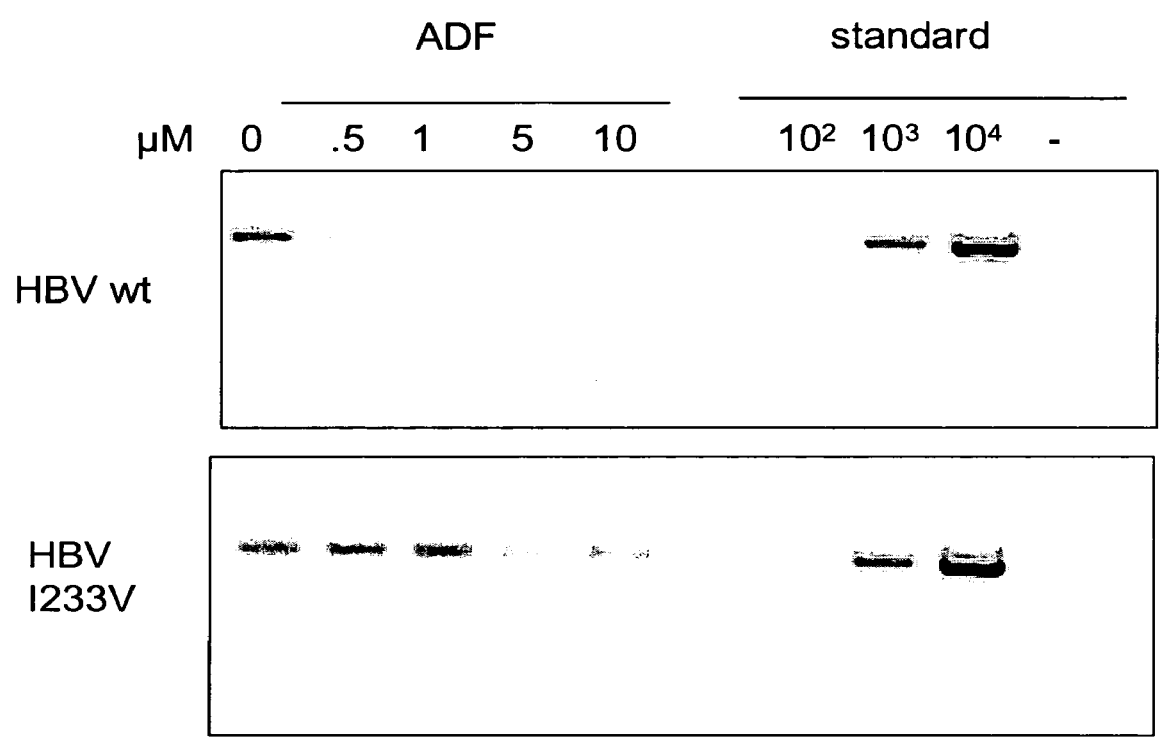

Rivkina M et al, Gene (1988), vol. 64, pp. 285-296, "Nucleotide sequence of integrated hepatitis B virus DNA and human flanking regions in the genome of the PLC/PRF/5 cell line" Figure 5.

Stoll-Becker et al, "Transcription of Hepatitis B Virus in Peripheral Blood Mononuclear Cells from Persistently Infected Patients", Journal of Virology, Jul. 1997, vol. 71, No. 7, pp. 5399-5407.

Stuyver et al, "Nomenclature for Antiviral-Resistant Human Hepatitis B Virus Mutations in the Polymerase Region", Hepatology 2001; 33:751-757.

Tatti et al, "Mutations in the conserved woodchuck hepatitis virus polymerase FLLA and YMDD regions conferring resistance to lamivudine", Antiviral Research 55 (2002) 141-150.

Tipples ("Mutation in HBV RNA-dependent DNA polymerase confers resistance to lamivudine in vivo" Hepatology 24(3): 714-717, Sep. 1996).

Torresi et al, "Restoration of Replication Phenotype of Lamivudine-Resistant Hepatitis B Virus Mutants by Compensatory Changes in the "Fingers" Subdomain of the Viral Polymerase Selected as a Consequence of Mutations in the Overlapping S Gene", Virology 299, 88-99 (2002).

Uchida T et al, J General Virology (1995), vol. 45, pp. 247-252, Complete nucleotide sequences and the characteristics of two hepatitis B virus mutants causing serologically negtive acute or chronic hepatitis B: p. 249.

Uchida,T. et al. GenBank Accession No. D50489, Title: "Direct Submission" Submitted (May 8, 1995) http://www.ncbi.nlm.nih.gov/entrez/viewer.fcgi?db=nuccore&id=807711.

Vaudin M et al, J. General Virology (1988), vol. 69, pp. 1383-1389, "The complete nucleotide sequence of the genome of a hepatitis B virus isolated from a naturally infected chimpanzee" Figure 1.

Wakefield et al, "In Vitro Enzymatic Activity of Human Immunodeficiency Virus Type 1 Reverse Transcriptase Mutants in the Highly Conserved YMDD Amino Acid Motif Correlates with the Infectious Potential of the Proviral Genome", Journal of Virology, Nov. 1992, vol. 66, No. 11, pp. 6806-6812.

Wang GT et al, "Sequencing of hapatitis B virus DNA fragment coding major HBsAg of escape mutant", Chung Hua I Hseuh Tsa Chih Jun. 1994 74(6) pp. 355-357, 391 (PubMed English Abstract PMID 7994645).

Weiss et al, "The HBV-Producing Cell Line HepG2-4A5: A new in vitro system for studying the regulation of HBV replication and for screening anti-hepatitis B virus drugs", Virology 216:214-218, Feb. 1, 1996.

Werle et al "Evolution of hepatitis B virus load and viral genome sequence during adefovir dipivoxil therapy" 2004, Journal of Viral Hepatitis, vol 11, No. 1, pp. 74-83.

Yamamoto et al, "Naturally Ocurring Escape Mutants of Hepatitis B Virus with . . . ", Journal of Virology, vol. 68, No. 4, Apr. 1994, pp. 2671-2676.

Yan, L. et al, Accession No. Q9IF40, submitted (Jun. 2000), title: "Direct Submission", http://www.ncbi.nlm.nih.gov.

Blum, "Variants of Hepatitis B, C and D Viruses: Molecular Biology and Clinical Significance", Digestion (1995); 56:85-95.

Kidd-Ljunggren, "Variability in Hepatitis B Virus DNA: Phylogenetic, Epidemiological and Clinical Implications", Scand J Infect Dig 28:111-116 (1996).

Kan Tan Sui, "Escape Mutants of HBs" (1993), 27(4), pp. 555-562.

H. Uetake Ed., Virology, 4th Ed., ver.1, Rikougaku-sha (publ.), Jul. 10, 2002, p. 452 (in Japanese) (Relevance noted in Doc. No. 61).

Aoyama & Partners letter dated Feb. 15, 2007, relating to Japanese Patent Application No. 521944/1998 (4 pages).

Aoyama & Partners letter dated Jan. 25, 2007, relating to Japanese Patent Application No. 521944/1988 (2 pages).
Aoyama & Partners letter dated Jul. 23, 2007, relating to Japanese Patent Application No. 521944/1998 (1 page) with English translation of amended claims (2 pages) and Amendment filed Jul. 19, 2007, in response to Official Action (11 pages).

* cited by examiner

Patient 1

```
       V   L   S   S   S   S   S   S   C   C   Y   A   S   S   S   C   W   F   F   W   T   I   K   V   C   C   P   C   V   L   *   F   Q  .    SEQ ID 11
  1  GCGTTTATC ATCTTCCTCT TCATCCTGCT GCTATGCCTC ATCTTCTTGT TGTTCTTCT GGACTATCAA GGTATGTTGC CCGTGTGTCC TCTAATTCCA  SEQ ID 1
     CGCAAAATAG TAGAAGGAGA AGTAGGACGA CGATACGGAG TAGAAGAACA ACCAAGAAGA CCTGATAGTT CCATACAACG GGCACACAGG AGATTAAGGT  SEQ ID 2

.   D   L   R   P   P   V   R   D   H   A   E   P   A   R   L   L   L   K   E   P   L   C   I   P   P   V   A   V   P   N   L   R   T      SEQ ID 11
 101 GGATCTCCGA CCACCAGTAC GGGACCATGC AGAACCTGCA CGACTATTGC TCAAGGAACC TCTATGTATC CCTCCTGTTG CTGTACCAAA CCTTCGGACG  SEQ ID 1
     CCTAGAGGCT GGTGGTCATG CCCTGGTACG TCTTGGACGT GCTGATAACG AGTTCCTTGG AGATACATAG GGAGGACAAC GACATGGTTT GGAAGCCTGC  SEQ ID 2

E   I   A   P   V   F   P   S   I   I   L   G   F   R   K   I   P   M   G   V   G   L   S   P   F   L   L   A   Q   F   T   S   A   I  .    SEQ ID 11
 201 GAAATTGCAC CTGTATTCCC ATCCATCATC CTGGGCTTTC GGAAAATTCC TATGGGAGTG GGCCTCAGCC CGTTTCTCCT GGCTCAGTTT ACTAGTGCCA  SEQ ID 1
     CTTTAACGTG GACATAAGGG TAGGTAGTAG GACCCGAAAG CCTTTTAAGG ATACCCTCAC CCGGAGTCGG GCAAAGAGGA CCGAGTCAAA TGATCACGGT  SEQ ID 2

.   C   S   V   R   R   A   F   P   H   C   L   A   F   S   Y   M   D   D   V   L   G   A   K   S   V   Q   H   L   E   A   L  .           SEQ ID 11
 301 TTTGTTCAGT GGTTCGTAGG GCTTTCCCCC ACTGTTTGGC TTTCAGTTAT ATGGATGATG TGGTATTGGG GGCCAAGTCT GTACAGCATC TTGAGGCCCT  SEQ ID 1
     AACAAGTCA CCAAGCATCC CGAAAGGGGG TGACAAACCG AAAGTCAATA TACCTACTAC ACCATTAACCC CCGGTTCAGA CATGTCGTAG AACTCCGGGA  SEQ ID 2

.   F   T   A   V   T   N   F   L   L   S   L   G   V   H   L   N   P   N   K   T   K                                                       SEQ ID 11
 401 TTTTACCGCT GTTACCAATT TTCTTTTGTC TTTGGGTGTA CATTTAAACC CTAACAAAAC AAAAA                                        SEQ ID 1
     AAAATGGCGA CAATGGTTAA AAGAAAACAG GTAAATTTGG GATTGTTTTG TTTTT                                                    SEQ ID 2
```

FIGURE 2a

Patient 2 bADF

```
      A   F   Y   H   L   P   L   H   P   A   A   M   P   H   L   L   V   G   S   S   G   L   S   R   Y   V   A   R   L   S   S   N   S  .   SEQ ID 12
  1  CGGCGTTTA TCATCTTCCT CTGCTATGCC CTTCATCCTG CTGCTATGCC TCATCTTCTT GTTGGTTCTT CTGGACTATC AAGGTATGTT GCCCGTTTGT CCTCTAATTC     SEQ ID 3
     GCCGCAAAAT AGTAGAAGGA GAAGTAGGAC GACGATACGG AGTAGAAGAA CAACCAAGAA GACCTGATAG TTCCATACAA CGGGCAAACA GGAGATTAAG              SEQ ID 4

.   R   I   F   N   H   Q   H   G   T   M   Q   N   L   H   D   Y   C   S   R   N   L   Y   V   S   L   L   L   Y   Q   T   F   G      SEQ ID 12
 101  CAGGATCTTC AACCACCAGC ACGGGACCAT GCAGAACCTG CACGACTATT GCTCAAGGAA CCTCTATGTA TCCCTCCTGT TGCTGTACCA AACCTTCGGA              SEQ ID 3
      GTCCTAGAAG TTGGTGGTCG TGCCCTGGTA CGTCTTGGAC GTGCTGATAA CGAGTTCCTT GGAGATACAT AGGGAGGACA ACGACATGGT TTGGAAGCCT              SEQ ID 4

R   K   L   H   L   Y   S   H   P   I   I   L   G   F   R   K   I   P   M   G   V   G   L   S   P   F   L   L   A   Q   F   T   S   A  .  SEQ ID 12
 201  CGGAAATTGC ACCTGTATTC CCATCCCATC ATCCTGGGCT TTCGGAAAAT TCCTATGGGA GTGGGCCTCA GCCCGTTTCT CCTGGCTCAG TTTACTAGTG              SEQ ID 3
      GCCTTTAACG TGGACATAAG GGTAGGGTAG TAGGACCCGA AAGCCTTTTA AGGATACCCT CACCCGGAGT CGGGCAAAGA GGACCGAGTC AAATGATCAC              SEQ ID 4

.   I   C   S   V   V   R   R   A   F   P   H   C   L   A   F   S   Y   I   D   D   V   V   L   G   A   K   S   V   Q   H   L   E   S  .  SEQ ID 12
 301  CCATTTGTTC AGTGGTTCGT AGGGCTTTCG CCCACTGTTT GGCTTTCAGT TATATTGATG ATGTGGTATT GGGGGCCAAG TCTGTACAGC ATCTTGAGTC              SEQ ID 3
      GGTAAACAAG TCACCAAGCA TCCCGAAAGG GGGTGACAAA CCGAAAGTCA ATATAACTAC TACACCATAA CCCCGGTTC AGACATGTCG TAGAACTCAG               SEQ ID 4

.   L   F   T   A   V   T   N   F   L   L   S   L   G   V   H   L   N   P   N   K   T   K   R   W   G   Y   S   L   N   F   M   G   Y      SEQ ID 12
 401  CCTTTTACC GCTGTTACCA ATTTCTTT GTCTTTGGGT GTACATTAA CCCTAACAA AACAAAAAGA TGGGGTTACT CTTTAAATTT CATGGGCTAT                  SEQ ID 3
      GGAAAAATGG CGACAATGGT TAAAAGAAAA CAGAAACCCA CATGTAAATT GGGATTGTT TTGTTTTTCT ACCCCAATGA GTACCCGATA                         SEQ ID 4

V   I   G   C   Y   G   S   L   P   Q   D   H   I   I   Q   K   I   K   E                                                 SEQ ID 12
 501  GTTATTGGAT GTTATGGGTC CTTGCCACAA GATCACATTA TTCAGAAAAT CAAAGAA                                                            SEQ ID 3
      CAATAACCTA CAATACCCAG GAACGGTGTT CTAGTGTAAT AAGTCTTTTA GTTTCTT                                                            SEQ ID 4
```

FIGURE 2b

Patient 2 pADF

```
       A   F   Y   H   L   P   L   H   P   A   A   M   P   H   L   L   V   G   S   S   G   L   S   R   Y   V   A   R   L   S   S   N   S   .
  1  CGGCGTTTTA TCATCTTCCT CTTCATCCTG CTGCTATGCC TCATCTTCTT GTTGGTTCTT CTGGACTATC AAGGTATGTT GCCCGTTTGT CCTCTAATTC    SEQ ID 13
     GCCGCAAAAT AGTAGAAGGA GAAGTAGGAC GACGATACGG AGTAGAAGAA CAACCAAGAA GACCTGATAG TTCCATACAA CGGGCAAACA GGAGATTAAG    SEQ ID 5
                                                                                                                    SEQ ID 6

.   R   I   F   N   H   Q   H   G   T   M   Q   N   L   H   D   Y   C   S   R   N   L   Y   V   S   L   L   L   L   Y   Q       T   F   G
 101  CAGGATCTTC AACCACCAGC ACGGGACCAT GCAGAACCTG CACGACTATT GCTCAAGGAA CCTCTATGTA TCCCTCCTGT TGCTGTACCA AACCTTCGGA    SEQ ID 13
     GTCCTAGAAG TTGGTGGTCG TGCCCTGGTA CGTCTTGGAC GTGCTGATAA CGAGTTCCTT GGAGATACAT AGGGAGGACA ACGACATGGT TTGGAAGCCT    SEQ ID 5
                                                                                                                    SEQ ID 6

R   K   L   H   L   Y   S       H   P   I   I   L   G   F   R   K   I       P   M   G       V   G   L   S   P   F   L   L   A   Q       F   T   S   A   .
 201  CGGAAATTGC ACCTGTATTC CCATCCCATC ATCCTGGGCT TTCGGAAAAT TCCTATGGGA GTGGGCCTCA GCCCGTTTCT CCTGGCTCAG TTTACTAGTG    SEQ ID 13
     GCCTTTAACG TGGACATAAG GGTAGGGTAG TAGGACCCGA AAGCCTTTTA AGGATACCCT CACCCGGAGT CGGGCAAAGA GGACCGAGTC AAATGATCAC    SEQ ID 5
                                                                                                                    SEQ ID 6

.   I   C   S       V   V   R       R   A   F   P       H   C   L       A   F   S       Y   M   D   D   D   V   V   L       G   A   K       S   V   Q   H       L   E   S   .
 301  CCATTTGTTC AGTGGTTCGT AGGGCTTTCC CCCACTGTTT GGCTTTCAGT TATATGGATG ATGTGGTATT GGGGGCCAAG TCTGTACAGC ATCTTGAGTC    SEQ ID 13
     GGTAAACAAG TCACCAAGCA TCCCGAAAGG GGGTGACAAA CCGAAAGTCA ATATACCTAC TACACCATAA CCCCCGGTTC AGACATGTCG TAGAACTCAG    SEQ ID 5
                                                                                                                    SEQ ID 6

.   L   F   T       A   V   T   N       F   L   L       S   L   G       V   H   L   N       P   N   K       T   K   R       W   G   Y   S       L   N   F       M   G   Y
 401  CCTTTTACC GCTGTTACCA ATTTTCTTTT GTCTTTGGGT GTACATTTAA ACCCTAACAA AACAAAAAGA TGGGGTTACT CTTTAAATTT CATGGGCTAT    SEQ ID 13
     GGAAAAATGG CGACAATGGT CGACAATGGT CAGAAACCCA CATGTAAATT TGGGATTGTT TTGTTTTTCT ACCCCAATGA GAAATTTAAA GTACCCGATA    SEQ ID 5
                                                                                                                    SEQ ID 6

V   I   G   C       Y   G   S       L   P   Q       D   H   I   I       Q   K   I       K   E
 501  GTTATTGGAT GTTATGGGTC CTTGCCACAA GATCACATTA TTCAGAAAAT CAARGAA                                                  SEQ ID 13
     CAATAACCTA CAATACCCAG GAACGGTGTT CTAGTGTAAT AAGTCTTTTA GTTTCTT                                                   SEQ ID 5
                                                                                                                    SEQ ID 6
```

FIGURE 2c

Patient 3 bADF

```
        I  Y  S  L     X  P  A     A  M  P     H  L  L  V     G  S  S     G  L  S     R  Y  V  A     R  L  S     S  N  S     R  I  F  N  .    SEQ ID 14
   1  ATATATTCTC TTCNNCCTGC TGCTATGCCT CATCTTCTTG TTGGTTCTTC TGGACTATCA AGGTATGTTG CCCGTTTGTC CTCTAATTCC AGGATCTTCA           SEQ ID 7
      TATATAAGAG AAGNNGGACG ACGATACGGA GTAGAAGAAC AACCAAGAAG ACCTGATAGT TCCATACAAC GGGCAAACAG GAGATTAAGG TCCTAGAAGT           SEQ ID 8

.  H  Q  H     G  T  M     Q  N  L  H     D  Y  C     S  R  N     L  Y  V  S     L  L  L     L  Y  Q     T  F  G  R     K  L  H  .    SEQ ID 14
 101  ACCACCAGCA CGGGACCATG CAGAACCTGC ACGACTATTG CTCAAGGAAC CTCTATGTAT CCCTTCTGTT GCTGTACCAA ACCTTCGGAC GGAAATTGCA           SEQ ID 7
      TGGTGGTCGT GCCCTGGTAC GTCTTGGACG TGCTGATAAC GAGTTCCTTG GAGATACATA GGGAAGACAA CGACATGGTT TGGAAGCCTG CCTTTAACGT           SEQ ID 8

.  L  Y  S     H  P  I  I     L  G  F     R  K  I     P  M  G  L     G  L  S     P  F  L     L  A  Q  F     T  S  A     I  C  S  .    SEQ ID 14
 201  CCTGTATTCC CATCCCATCA TCCTGGGCTT TCGGAAAATT CCTATGGGAC TGGGCCTCAG CCCGTTTCTC CTGGCTCAGT TTACTAGTGC CATTTGTTCA           SEQ ID 7
      GGACATAAGG GTAGGGTAGT AGGACCCGAA AGCCTTTTAA GGATACCCTG ACCCGGAGTC GGGCAAAGAG GACCGAGTCA AATGATCACG GTAAACAAGT           SEQ ID 8

V  V  R  R     A  F  P     H  C  L     A  F  S  Y     I  D  D     V  V  L     G  A  K  S     V  Q  H     L  E  S     L  F  T  A  .    SEQ ID 14
 301  GTGGTTCGTA GGGCTTTCCC CCACTGTTTG GCTTTCAGTT ATATTGATGA TGTGGTATTG GGGGCCAAGT CTGTACAGCA TCTTGAGTCC CTTTTTACCG           SEQ ID 7
      CACCAAGCAT CCCGAAAGGG GGTGACAAAC CGAAAGTCAA TATAACTACT ACACCATAAC CCCCGGTTCA GACATGTCGT AGAACTCAGG GAAAAATGGC           SEQ ID 8

.  V  T  N     F  L  L     S  L  G  V     H  L  N     P  N  K     T  K  X  W     G  X  X     X  X  X                               SEQ ID 14
 401  CTGTTACCAA TTTTCTTTTG TCTTTGGGTG TACATTTAAA CCCTAACAAA ACAAAAGNAT GGGGGTANNN NNNNNNNT                                  SEQ ID 7
      GACAATGGTT AAAAGAAAAC AGAAACCCAC ATGTAAATTT GGGATTGTTT TGTTTTCNTA CCCCCATNNN NNNNNNNA                                   SEQ ID 8
```

FIGURE 2d

Patient 3 pADF

```
     I  Y  S  L  X  P  A  A  M  P  H  L  L  V  G  S  S  G  L  S  R  Y  V  A  R  L  S  S  N  S  R  I  F  N  .    SEQ ID 15
  1  ATATATTCTC TTCNNCCTGC TGCTATGCCT CATCCTCCTG TTGGTTCTTC TGGACTATCA AGTATGTGTG CCCGTTTGTC CTCTAATTCC AGGATCTTCA   SEQ ID 9
     TATATAAGAG AAGNNGGACG ACGATACGGA GTAGAAGAAC AACCAAGAAG ACCTGATAGT TCCATACAAC GGGCAAACAG GAGATTAAGG TCCTAGAAGT   SEQ ID 10

.  H  Q  H  G  T  M  Q  N  L  H  D  Y  C  S  R  N  L  Y  V  S  L  L  L  L  Y  Q  T  F  G  R  K  L  H  .    SEQ ID 15
101  ACCACCAGCA CGGGACCATG CAGAACCTGC ACGACTATTG CTCAAGGAAC CTCTATGTAT CCCTTCTGTT GCTGTACCAA ACCTTCGGAC GGAAATTGCA   SEQ ID 9
     TGGTGGTCGT GCCCTGGTAC GTCTTGGACG TGCTGATAAC GAGTTCCTTG GAGATACATA GGGAAGACAA CGACATGGTT TGGAAGCCTG CCTTTAACGT   SEQ ID 10

.  L  Y  S  H  P  I  I  L  G  F  R  K  I  P  M  G  V  G  L  S  P  F  L  L  A  Q  F  T  S  A  I  C  S      SEQ ID 15
201  CCTGTATTCC CATCCCATCA TCCTGGGCTT TCGGAAAATT CCTATGGGAG TGGGCCTCAG CCCGTTTCTC CTGGCTCAGT TTACTAGTGC CATTTGTTCA   SEQ ID 9
     GGACATAAGG GTAGGGTAGT AGGACCCGAA AGCCTTTTAA GGATACCCTC ACCCGGAGTC GGGCAAAGAG GACCGAGTCA AATGATCACG GTAAACAAGT   SEQ ID 10

V  V  R  R  A  F  P  H  C  L  A  F  S  Y  I  D  D  V  V  L  G  A  K  S  V  Q  H  L  E  S  L  F  T  A  .    SEQ ID 15
301  GTGGTTCGTA GGGCTTTCCC CCACTGTTTG GCTTTCAGTT ATATTGATGA TGTGGTATTG GGGGCCAAGT CTGTACAGCA TCTTGAGTCC CTTTTTACCG   SEQ ID 9
     CACCAAGCAT CCCGAAAGGG GGTGACAAAC CGAAAGTCAA TATAACTACT ACACCATAAC CCCCGGTTCA GACATGTCGT AGAACTCAGG GAAAAATGGC   SEQ ID 10

.  V  T  N  F  L  L  S  L  G  V  H  L  N  P  N  K  T  K  X                                                   SEQ ID 15
401  CTGTTACCAA TTTTCTTTTG TCTTTGGGTG TACATTTAAA CCCTAACAAA ACAAAAGNAT                                              SEQ ID 9
     GACAATGGTT AAAAGAAAAC AGAAACCCAC ATGTAAATTT GGGATTGTTT TGTTTTCNTA                                              SEQ ID 10
```

FIGURE 2e

| | | |
|---|---|---|
| P1 | GVGLSPFLLAQFTSAICSVVRRAFPHCLAFSYMDDVVLGAKSVQHLEALFTAVTNFLLSLGVHLNPNKTK | seq id 16 |
| P2 bADF | GVGLSPFLLAQFTSAICSVVRRAFPHCLAFSYIDDVVLGAKSVQHLESLFTAVTNFLLSLGVHLNPNKTK | seq id 17 |
| P2 pADF | GVGLSPFLLAQFTSAICSVVRRAFPHCLAFSYMDDVVLGAKSVQHLESLFTAVTNFLLSLGVHLNPNKTK | seq id 18 |
| P3 bADF | GLGLSPFLLAQFTSAICSVVRRAFPHCLAFSYIDDVVLGAKSVQHLESLFTAVTNFLLSLGVHLNPNKTK | seq id 19 |
| P3 pADF | GVGLSPFLLAQFTSAICSVVRRAFPHCLAFSYIDDVVLGAKSVQHLESLFTAVTNFLLSLGVHLNPNKTK | seq id 20 |
| *wt D* | GVGLSPFLLAQFTSAICSVVRRAFPHCLAFSYMDDVVLGAKSVQHLESLFTAVTNFLLSLGIHLNPNKTK | seq id 21 |

LMV 173 — LMV 180 — ADF? 181 — LMV? 204 — ADF 217 219 — ADF 233 236

VARIANTS OF HEPATITIS B VIRUS RESISTANT AGAINST SOME NUCLEOSIDE ANALOGUES, BUT SENSITIVE TO OTHERS, AND USES THEREOF

This application claims benefit of U.S. Provisional Application No. 60/661,483 filed 15 Mar. 2005, the entire contents of which is hereby incorporated by reference. The application also claim benefit of EP 05102014.7, filed Mar. 15, 2005.

The present invention relates to the field of Hepatitis B virus (HBV, also indicated with HBV virus) variants exhibiting a reduced sensitivity to particular agents. More particularly, the present invention relates to the field of diagnosing the susceptibility of an HBV sample to antiviral drugs used to treat HBV infection and to a method and/or assay for the rapid and reliable detection of drug-induced mutations in the HBV genes allowing the simultaneous characterization of a range of codons involved in drug resistance.

HBV is a small-enveloped DNA virus of approximately 3200 bp length belonging to the family of the hepadnaviruses. The virus replicates via an RNA intermediate and utilises reverse transcription in its replication strategy (Summers, 1982). The HBV genome is of a complex nature having a partially double stranded DNA structure with overlapping open reading frames (ORFs) being (i) the preC/C ORF encoding the secreted e antigen (HBeAg) and nucleocapsid core protein (HBcAg), respectively; (ii) the P ORF encoding the viral polymerase/reverse transcriptase; (iii) the preS1/preS2/S ORF encoding the viral envelope proteins, large, middle and small s antigen (HBsAg), respectively; and (iv) the X ORF encoding a transcriptional trans-activator protein encoding surface, core, polymerase and X genes.

Hepatitis B viruses exhibit a large genetic variability in their genomes, with currently seven HBV genotypes (A to G) being recognized (Stuyver et al., 2001; Stuyver et al., 2000). The virus, which is spread through contact with infected blood, can cause debilitating disease conditions and can lead to acute liver failure. Although most adults can fight off an infection without treatment, hepatitis B infection may develop into a chronic form. Actually, about 400 million people world-wide are chronically infected with HBV and approximately 15 to 40% of chronic HBV carriers are expected to progress to cirrhosis and end-stage liver disease. Without treatment the prognosis for these patients is poor, consequently the development of effective antiviral therapy for HBV remains an important goal. The principle objective of therapy is to control the replication of HBV and induce the remission of hepatic disease in order to stop progression to cirrhosis and hepatic cancer. Treatment is indicated for patients with active inflammation, elevated alanine aminotransferase (ALT) levels due to the destruction of liver cells, and levels of HBV DNA (viral replication levels) higher than 100,000 copies/ml.

Current drugs approved for the treatment of chronic hepatitis B are the alfa-interferons, and nucleoside analogues or combinations of the drugs. A nucleoside analogue is a chemically engineered nucleotide that acts as a substitute building block in the viral replication process, inhibiting the replication of HBV.

Interferon (IFN) therapy has been shown to be partially effective only in a small group of carriers (Lok, 1994) and it is also limited due to severe side effects. This relative failure of IFN-α for the treatment of chronic HBV infection has prompted the search for further therapeutic agents and regimes. In particular, a number of nucleoside analogues has been shown to inhibit hepadnaviral replication via inhibition of the hepadnaviral DNA polymerase/reverse transcriptase. Some of these compounds have already been withdrawn from clinical use due to toxicity (lobucavir) or lack of efficacy (famciclovir) (De Clercq, 1999; Schinazi, 1997; Luscombe et al., 1996). At this moment, the most successful nucleoside analogue for treatment of chronic hepatitis B is without doubt the medically approved (−) enantiomer of 3'-thiacytidine (3TC or lamivudine (LMV)), (Jarvis et al., 1999). The drug has a potent antiviral activity against the virus, is well tolerated and has few adverse effects. However, long term therapy with lamivudine frequently is associated with the emergence of viral resistance. One of the common mutations that confer lamivudine resistance and reduce the in vitro replication efficiency of the virus is a methionine-to-isoleucine or methionine-to-valine substitution at codon 204 of the HBV RNA-dependent DNA (Ling R. et al., 1996; Bartholomew M. et al., 1997; Tipples G. A. et al., 1996). Besides the alteration of this Met-to-Val or to-Ile amino acid substitution (rtM204V/I) at the conserved YMDD motif, mutated genotypic patterns at other sites of the reverse trancriptase gene have been associated to lamivudine resistance. In particular, the leucine-to-methionine mutation at codon 180 (rtL180M) in the B-domain of the polymerase was reported to partially restore replication fitness as well as to augment drug resistance in vitro. In HBV/HIV co-infected patients the development of lamivudine resistance is more frequent than in HBV mono-infected patients, making a therapy alternative to lamivudine application indispensable (Benhamou et al., 2001; Benhamou et al., 2003; Benhamou et al., 2004; Dore G. J. et al., 2004).

Another nucleoside analogue applicable for the treatment of chronic hepatitis B is adefovir dipivoxil, the pro-drug of adefovir (ADF). Studies in vitro and in vivo have demonstrated that this drug is able to inhibit wild-type HBV strains as well as those showing lamivudine resistances. Therefore, ADF may serve as an alternative therapy for treatment of chronic HBV infection in cases where lamivudine resistance has occurred. Hitherto, ADF passed successfully clinical phase III studies (Westland C E et al, 2003.). Two mutations mediating resistance to ADF have already been described. These mutations are located at codon 181 (B-domain) and at codon 236 (D-domain) of the reverse transcriptase gene and result in an amino acid substitution Ala to Val (rtA181V) and Asn to Thr (rtN236T), respectively (Angus P. et al., 2003; Yang H. et al., 2003; WO 2003/087352; WO 2004/031224). The frequency of the mutation rtA181V is about 2.5% with a hitherto unknown clinical relevance, whereas 1.7-2.5% of the adefovir treated patients reveals the resistance mutation rtN236T.

Recently published studies by Perrillo et al. (2004) as well as by Peters et al (2004) demonstrate that approximately 85% to 92% of patients with lamivudine resistance will have a decrease in their HBV DNA level by greater than or equal to two logs while receiving ADF. This implies that 8-15% of patients does not achieve a significant reduction in HBV DNA levels when ADF is added to the therapy. Therefore, there is a precedent for a subgroup of patients with lamivudine resistant HBV that will not achieve a virologic response with ADF therapy. The reason for the non-responsiveness to ADF remains unclear.

From the previous, it seems there is a need to monitor the emergence or presence of HBV variants exhibiting a reduced sensitivity to particular agents, in order to screen for and/or develop and/or design other agents having properties suitable for making them useful in new therapeutic regimes. In accordance with the present invention, the inventors have identified variants of HBV with mutations in the HBV DNA polymerase gene which reduce the sensitivity of HBV to nucleoside analogues but which are sensitive to one or more other nucleoside analogues.

SUMMARY OF THE INVENTION

The present invention aims to solve the problem of inadequate monitoring of the emergence or presence of HBV variants exhibiting a reduced sensitivity to nucleoside analogues.

The present invention relates to isolated HBV variants that comprise at least one nucleotide mutation in the DNA polymerase gene, wherein said nucleotide mutations result in at least one amino acid substitution in the HBV polymerase and wherein said variant exhibits a decreased sensitivity to the nucleoside analogue ADF and/or LMV and/or their combination.

The present invention further relates to isolated polynucleic acids from these HBV variants, which isolated polynucleic acids comprise a nucleotide mutation that results in at least one amino acid substitution and/or deletion in the polymerase gene and which nucleotide mutation leads to a reduced sensitivity to the nucleotide analogue ADF and/or LMV and/or a their combination; and to a fragment of said HBV polynucleic acid comprising said nucleotide mutation.

The present invention further relates to expression products from these isolated polynucleic acids and to a fragment thereof.

Further aspects of the invention relate to compositions that comprise HBV variants or polynucleic acid or expression products of the present invention, which preferably find their application in the monitoring and/or identification of HBV variants.

Another aspect of the invention relates to the use of the isolated HBV variants and/or their polynucleic acids and/or expression products and/or compositions as described above in clinical decision making. In particular, HBV variants or polynucleic acids or expression products or compositions of the present invention are used in a process for the selection of at least one non-cross resistant anti-HBV drug. In particular, HBV variants or polynucleic acids or expression products or compositions are used in a process for the detection of an HBV variant polynucleic acid.

The present invention further relates to a process for the treatment of HBV infection comprising administering a nucleoside analogue to a subject infected with HBV, determining whether the subject is infected with an HBV variant as described, and if so, administering to the subject at least one non-cross resistant anti-HBV drug.

Further included in the invention are methods aimed to detect the presence of the HBV variants according to the invention in a biological sample. Said method comprises the step of detecting therein the presence of an HBV polynucleic acid or fragment thereof.

Finally, the present invention relates to a diagnostic kit detecting the presence of an HBV variant in a biological sample and/or for detecting resistance to an antiviral drug of an HBV present in a biological sample. Furthermore, a method has been provided for screening for drugs active against an HBV comprising a polynucleic acid as indicated above.

Furthermore an oligonucleotide capable of discriminating, in an HBV polynucleic acid or a fragment thereof, a new codon 233 encoding an amino acid different from isoleucine has been provided.

FIGURE LEGENDS

FIG. 1. Schematic presentations of the history of patients 1, 2 and 3.

The X-axis represents the time line in weeks starting at week 10. At the top of the schemes parallel with the X-axis the successive treatments of HBV-infected patients 1, 2 and 3 are indicated. On the Y-axis, the viral DNA load in ge/ml is represented in a logarithmic way. The HBV load was quantified using the Versant assay (Bayer).

FIG. 2 (2a, 2b, 2c, 2d and 2e): Alignment of HBV DNA polymerase sequences of patients 1, 2 and 3

Fragments of the HBV DNA polymerase/reverse transcriptase nucleotide sequences, indicated by SEQ ID NO 1 (forward) and 2 (reverse) of patient 1 (equal before and after ADF teatment), indicated by SEQ ID no 3 (forward) and 4 (reverse) of patient 2 before ADF therapy (bADF) and by SEQ ID no 5 (forward) and 6 (reverse) of patient No. 2 after ADF therapy (pADF), indicated by SEQ ID no 7 (forward) and 8 (reverse) of patient No. 3 before ADF therapy (bADF) and by SEQ ID no 9 (forward) and 10 (reverse) of patient No. 3 after ADF therapy (pADF). The corresponding amino acid sequences have been indicated by 11, 12, 13, 14 and 15, respectively.

FIG. 3: Alignment of HBV DNA polymerase sequences.

Aligned are fragments of the HBV D DNA polymerase/reverse transcriptase amino acid sequence wt indicated by seq id 21 (EMBL access nr Y07587) with HBV DNA polymerase/reverse transcriptase amino acid sequences as described in FIG. 2 (SEQ ID's 16, 17 and 19), and also fragments of HBV D DNA polymerase/reverse transcriptase amino acid sequences from the same patients after adefovir (pADF) therapy, indicated as SEQ ID's 16, 18 and 20.

Figure 4:
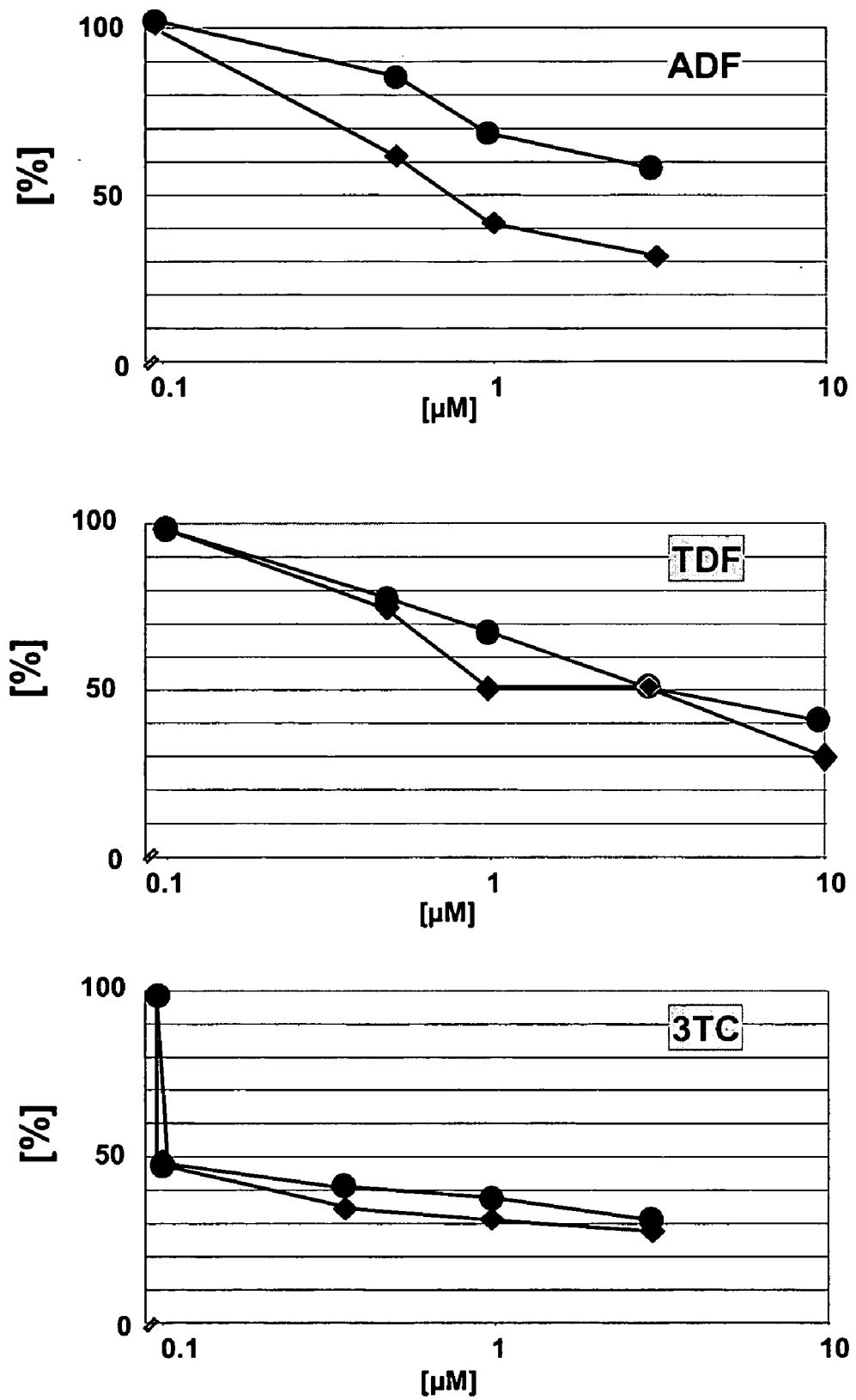

FIG. 4: Inhibition of intracellular HBV DNA synthesis in vitro.

Inhibition of intracellular HBV DNA synthesis in vitro by increasing concentrations of adefovir (ADF), tenofovir (TNF), and lamivudine (3TC). Southern blots of extracts obtained 6 days after transfection were quantitatively evaluated by phosphoimaging and related to untreated controls. wt HBV genotype D (♦) and the rtI233V variant (●).

FIG. 5: HBV DNA in the presence of increasing adefovir concentrations.

HBV DNA of the wild type (wt) or variant secreted to the supernatant of transfected cells in the presence of increasing adefovir concentrations. The DNA was extracted, amplified by PCR, and quantified against a standard plasmid control.

DETAILED DESCRIPTION OF THE INVENTION

In accordance with the present invention, the inventors have identified variants of HBV in patients chronically infected with HBV that were virologically non-responsive to ADF or ADF-comprising therapy and/or LMV or LMV-comprising therapy and/or a combination of these anti-HBV agents. Particularly, the sensitivity to other nucleoside analogues as for instance tenofovir (TDF) did not decrease. Sequence analysis of isolated HBV DNA revealed the emergence of novel nucleic acid polymorphisms in the HBV polymerase.

More particularly, the present invention provides an improved diagnosis of the susceptibility of an HBV sample to antiviral drugs used to treat HBV infection and in a method and/or improved assay for the rapid and reliable detection of drug-induced mutations in the HBV genes allowing the simultaneous characterization of a range of codons involved in drug resistance which codons include the novel nucleic acid polymorphisms.

Throughout the invention as described below various publications are referenced. The contents of said publications are hereby incorporated by reference into the current application. Said publications are meant to describe more fully the art to which the current invention pertains.

A first aspect of the invention is related to isolated HBV variants that comprise at least one nucleotide mutation in the DNA polymerase gene, wherein said nucleotide mutation results in at least one amino acid substitution in domain B of the polymerase gene and wherein said variant exhibits a decreased sensitivity to a nucleoside analogue and/or other antiviral drugs against HBV except of tenovofir. Preferred HBV variants comprise at least one nucleotide mutation that results in at least one amino acid substitution of the alanine at codon position 233 of the polymerase gene, more in particular at least one nucleotide mutation which results in an isoleucine to valine amino acid substitution at codon 233 of the polymerase gene, also indicated by rtI233V. The isolated HBV variant according to the invention preferably exhibits a decreased sensitivity to a nucleoside analogue, preferably the nucleoside analogue is Adefovir and/or Lamivudine.

The present invention also covers isolated HBV variants that comprise besides a mutated 233 codon, especially rtI233V, further mutated genotypic patterns at other sites of the HBV polymerase. Preferably, the further mutation results in an altered amino acid sequence in any of the different domains of the polymerase gene. These include known amino acid alterations associated with drug resistance. Thus, the present invention extends to isolated HBV variants that comprise one rtI233X, especially rtI233V substitution in domain D of the polymerase gene together with at least one further mutation that comprises one or more further nucleotide mutations in the DNA polymerase gene chosen from the group consisting of a nucleotide at codon 173, at codon 204 and at codon 219 wherein said further nucleotide mutation at codon position 173 of the polymerase gene results in the amino acid substitution of the valine to any amino acid other than valine, at codon position 204 of the polymerase gene results in the amino acid substitution of the methionine to any amino acid other than methionine, and at codon position 219 of the polymerase gene results in the amino acid substitution of the serine to any amino acid other than serine. Preferably, said further nucleotide mutation at codon 204 results in the amino acid substitution of methionine to isoleucine, at codon 173 results in the amino acid substitution of the valine to leucine and at codon 219 results in the amino acid substitution of the serine to alanine.

The term "mutation" has to be read in its broadest context and includes multiple mutations. It is to be understood that the present invention extends to isolated HBV variants that comprises at least one and/or two and/or three and/or four and/or five and/or six nucleotide mutations in the DNA polymerase gene, wherein said nucleotide mutations result in at least one and/or two and/or three and/or four and/or five and/or six amino acid substitutions, one substitution being the isoleucine at codon position 233 in domain D of the polymerase gene into any amino acid other than isoleucine, preferably the substitution of isoleucine into a valine.

"Isolated" when used in reference to the HBV variants and/or HBV polynucleic acids and/or expression products of this invention means that the variant or polynucleic acid have undergone at least one purification step away from naturally occurring body fluid and/or tissue or that it is not present in its native environment. Alternatively, the variants may be maintained in isolated body fluid and/or tissue or may be in a polynucleic acid form. Typically, this means that the virus variant or polynucleic acid is free of at least one of the host proteins and/or host nucleic acids. In general, the isolated virus variant or polynucleic acid is present in an in vitro environment. "Isolated" does not mean that the virus variant or polynucleic acid must be purified or homogeneous, although such preparations do fall within the scope of the term. "Isolated" simply means raised to a degree of purity, to the extent required excluding product of nature and accidental anticipations from the scope of the claims. "Isolated" is meant to include any biological material taken either directly from an infected human being or animal, or after culturing (enrichment). "Biological material" may be e.g. expectorations of any kind, broncheolavages, blood, skin tissue, biopsies, sperm, lymphocyte blood culture material, colonies, liquid cultures, faecal samples, urine, etc. "Biological material" may also be artificially infected cell cultures or the liquid phase thereof.

Reference to "decreased" or "reduced" sensitivity in relation to a nucleoside analogue includes and encompasses a complete or substantial resistance to the nucleoside analogue as well as partial resistance and includes a replication rate or replication efficiency which is more than a wild-type in the presence of a nucleoside analogue. In one aspect, this is conveniently measured by an increase in viral load during treatment, or alternatively, there is no substantial decrease in HBV DNA viral load from pre-treatment HBV DNA levels during treatment (i.e., non-response to treatment). Particularly, the "decreased sensitivity" is in respect of ADF. Alternatively, the "decreased sensitivity" is in respect of LMV. Alternatively, the "decreased sensitivity" is in respect of both LMV and ADF. Alternatively, the "decreased sensitivity" is in respect to ADF and/or LMV and/or other nucleoside analogues and/or other antiviral drugs against HBV.

Many antiviral drugs against HBV (HBV antiviral drugs) are known and include: lobucavir, penciclovir or famciclovir, lamivudine (3TC; β-L-(−)-2',3'-dideoxy-3'-thiacytidine), interferon-α, adefovir dipivoxil (Bis-POM-PMEA) or adefovir (PMEA; 9-(2-phosphonyl-methoxyethyl)-adenine), entecavir (BMS 200475), emtricitabine [(−)FTC; (−)-β-L-2', 3'-dideoxy-5-fluoro-3'-thiacytidine], DXG [(−)-β-D-2,6-diaminopurine dioxolane], DAPD (diaminopurine dioxolane), clevudine (L-FMAU; 2'-fluoro-5-methyl-β-L-arabinofuranosyluracil), L-dT (β-L-thymidine), L-Fd4C (2',3'-dideoxy-2',3'-didehydro-β-L(−)-5 fluorocytidine), foscarnet, carbovir, racivir, tenofovir, ganciclovir, nevirapine, (−)BCH189 (Ono et al., 2001), QYL865 (Fu et al., 2000), thymosin-α, and HBIg, the antibody against HBsAg,. Two or more HBV antiviral drugs can be used in combination as well.

Not all HBV genomes have exactly the same length and the polymerase is likewise unequal, due to the presence of insertions or deletions within the linker or spacer domain between the terminal protein and catalytic components of the protein. To overcome this confusion, a group of investigators developed a genotype-independent numbering scheme for the polymerase. One possible way of indicating mutated codons in the HBV polymerase gene is according to Stuyver et al., 2001, where the methionine (M) in the YMDD locus of the catalytic C domain of polymerase is numbered rtM204 rather than 539, 549, 550 or 552. This numbering system will be used in the present patent application. Accordingly, mutations in the HBV DNA polymerase gene associated with nucleoside analogue treatment of chronic hepatitis B have been described in domain B as rtV173L, rtL180M, rtA181V, in domain C as rtM204I, rtM204V, rtM204S, rtL217R, rtS219A and in domain D as rtN236T.

Another aspect of the present invention relates to isolated polynucleic acids encoding the HBV variants of the present invention. These isolated polynucleic acids comprise a nucleotide mutation that results in at least one amino acid substitution and/or deletion in the HBV polymerase. In particular the invention relates to isolated polynucleic acids comprising a nucleotide mutation at codon 233 of the polymerase gene, more in particular comprising at least one nucleotide mutation which results in a substitution of isoleucine at codon 233 of the polymerase. More in particular the isolated polynucleic acids comprise a nucleotide mutation that results in an amino acid substitution rtI233V.

The present invention also covers isolated polynucleic acids that comprise besides rtI233V further mutated genotypic patterns at other sites of the HBV polymerase. Preferably, the further mutation results in an altered amino acid sequence in any of the different domains of the polymerase gene. These mutations include known amino acid alterations associated with drug resistance. Thus, the present invention extends to isolated polynucleic acids that comprise one mutation coding for the rtI233V substitution in domain D of the polymerase gene and at least one further mutation coding for one or more amino acid substitution chosen from the group consisting of rtV173L, rtL180M, rtA181V, rtM204I or rtM204V or M204S, rtL217R, rtS219A and rtN236T.

The present invention also covers isolated polynucleic acids that comprise besides a mutation coding for rtI233X, especially rtI233V further mutated genotypic patterns located in domain C of the polymerase gene. More preferably, the further nucleotide mutation results in the substitution of the Methionine at codon position 204 in domain C of the polymerase gene.

In particular isolated HBV variants are covered that comprises at least two nucleotide mutations in the DNA polymerase gene, wherein said nucleotide mutations result in at least two amino acid substitutions, one substitution of the isoleucine at codon position 233 in domain D of the polymerase gene and one substitution of the methionine at codon position 204 in domain C of the polymerase gene. The substitution of the methionine at codon position 204 is meant to include any amino acid other than methionine, preferably the substitution is into an isoleucine and/or a valine and/or a serine.

The exemplary polynucleic acids comprise nucleotide mutations in the DNA polymerase gene that code for the rtI233V substitution in domain D of the polymerase gene and especially the rtM204I substitution in domain C of the polymerase gene. In a specific embodiment, said isolated HBV polynucleic acid comprises a sequence chosen from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10. More specifically, said isolated HBV polynucleic acid is defined by a sequence chosen from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

Another aspect of the invention relates to fragments of the above-mentioned isolated polynucleic acid, which fragments comprise the described nucleotide mutations leading to a reduced sensitivity to a nucleoside analog and/or other anti-HBV agents. These fragments comprise at least the genotypic pattern that results in the rtI233V substitution.

In a further embodiment, said isolated HBV polynucleic acid thereof may be DNA, or RNA wherein T is replaced by U, or may be a synthetic polynucleic acid.

Polynucleic acids encoding the variants of this invention vary in length and may vary in selection of bases flanking the mutant residue codon. The length of the polynucleic acid is not critical provided that it is recognized to be part of a hepatitis B virus sequence for the purpose intended. Considerable sequence variation exists within the genome of the virus, and thus the nucleic acid sequences flanking the variant sites may vary considerably even in the naturally occurring sequences. Sufficient polynucleic acid need only be present to provide novelty and utility for the sequence encoding the variant, but otherwise the length of the sequence flanking the selected codon is not important. Typically the length of the sequence (including the variant codon) will be any integer from within the range of 9 to 200 bp, usually 12, 13, 14, 15, 16, 17, 18, 19, 20, 21, 22, 23, 24, to 25 bp. Also included are sequences sufficiently long to encode the entire variants and fragments further described below.

The "isolated polynucleic acid or fragment thereof" according to the invention is meant to comprise single-stranded polynucleic acids, double-stranded polynucleic acids or triplex-forming polynucleic acids obtained directly from a sample or obtained after duplication, multiplication or amplification. "Obtained" is, in the present context, meant to include isolation and/or purification and/or amplification of said polynucleic acids from a biological sample. The "sample" may be any biological material taken either directly from an infected human being or animal, or after culturing (enrichment). "Duplication, multiplication or amplification" is meant to include any nucleic acid produced by using any nucleic acid amplification method including any sequencing technique. Thus, any sequencing technique producing a nucleic acid molecule comprising any of said, or a combination of said nucleic acid polymorphisms is to be understood to be comprised in the term "duplication, multiplication or amplification".

The term "synthetic polynucleic acid" as referred to here is meant to be a single-stranded polynucleic acid, double-stranded polynucleic acid or triplex-forming polynucleic acid. Polynucleic acids can be made in vitro by means of a nucleotide sequence amplification method. If such an amplified polynucleic acid is double-stranded, conversion to a single-stranded molecule can be achieved by a suitable exonuclease given that the desired single-stranded polynucleic acid is protected against said exonuclease activity. Alternatively, polynucleic acids are derived from recombinant plasmids containing inserts including the corresponding polynucleotide sequences, if need by cleaving the latter out from the cloned plasmids upon using the adequate nucleases and recovering them, e.g. by fractionation according to molecular weight. Another means of making a synthetic polynucleic acid in vitro is comprised within any method of nucleic acid sequencing. Products of a sequencing reaction are thus clearly covered by the term "synthetic polynucleic acid". The polynucleic acids according to the present invention can also be synthesized chemically, for instance by applying the conventional phospho-triester or phosphoramidite chemistry.

"Nucleotide sequence (DNA or RNA) amplification" is meant to include all methods resulting in multiplication of the number of target nucleotide sequence copies. Nucleotide sequence amplification methods include the polymerase chain reaction (PCR; DNA amplification), strand displacement amplification (SDA; DNA amplification), transcription-based amplification system (TAS; RNA amplification), self-sustained sequence replication (3SR; RNA amplification), nucleic acid sequence-based amplification (NASBA; RNA amplification), transcription-mediated amplification (TMA; RNA amplification), Qβ-replicase-mediated amplification and run-off transcription.

The terms "polynucleotide", "polynucleic acid", "nucleic acid sequence", "nucleotide sequence", "nucleic acid molecule", "oligonucleotide", "probe" or "primer", when used herein refer to nucleotides, either ribonucleotides, deoxyribonucleotides, peptide nucleotides or locked nucleotides, or a combination thereof, in a polymeric form of any length or any shape (e.g. branched DNA). Said terms furthermore include double-stranded (ds) and single-stranded (ss) polynucleotides as well as triple-stranded polynucleotides. Said terms also include known nucleotide modifications such as methylation, cyclization and 'caps' and substitution of one or more of the naturally occurring nucleotides with an analog such as inosine or with nonamplifiable monomers such as HEG (hexethylene glycol).

Ribonucleotides are denoted as NTPs, deoxyribonucleotides as dNTPs and dideoxyribonucleotides as ddNTPs.

Nucleotides can generally be labeled radioactively, chemiluminescently, fluorescently, phosphorescently or with infrared dyes or with a surface-enhanced Raman label or plasmon resonant particle (PRP).

Modifications of nucleotides include the addition of acridine or derivatives thereof, Acrydite™, amine, biotin, BHQ-1™, BHQ-2™, BHQ-3™, borane dNTPs, carbon spacers (e.g. $C_3$, $C_6$, $C_7$, $C_9$, $C_{12}$ or $C_{18}$), cascade blue, cholesterol, coumarin or derivatives thereof, Cy3®, Cy3.5®, Cy5®, Cy5.5®, Cy7® DABCYL, dansylchloride, digoxigenin, dinitrophenyl, dual biotin, EDANS, 6-FAM, fluorescein, 3'-glyceryl, HEX, IAEDANS, inverted dA, inverted dG, inverted dC, inverted dG, IRD-700, IRD-800, JOE, La Jolla Blue, metal clusters such as gold nanoparticles, phenylboronic acid, phosphate psoralen, 3'- or 5'-phosphorylation, pyrene, 3' riboadenosine, 3' ribo-guanosine, 3' ribo-cytidine, (LC)Red640, (LC)Red705, rhodamine, ROX, thiol (SH), spacers, TAMRA, TET, AMCA-S®, SE, BODIPY®, Marina Blue®, Oregon Green®, Pacific Blue®, QSY7™, Rhodamine Green®, Rhodamine Red®, Rhodol Green®, tetramethylrhodamine, Texas Red®, Uni-Link $NH_2$-modifier, radiolabels (e.g. $^{125}I$, $^{131}I$, $^{35}S$, $^{14}C$, $^{32}P$, $^{33}P$, $^3H$) and nanoparticles.

Polynucleotide backbone and base modifications further include 2'-deoxyaristero-mecyin, methylphosphonate, 2'-OMe-methylphosphonate RNA, 2'-O-(2-methoxyethyl), phosphorothioate, alkylphosphorothiate, phosphoramidite, RNA, 2'-OMeRNA, 2-amino-dA, 2-aminopurine, 3'-(ddA), 3'dA(cordycepin), 7-deaza-dA, 8-Br-dA, 8-oxo-dA, $N^6$-Me-dA, abasic site (dSpacer), biotin dT, 2'-OMe-5Me-C, 2'-OMe-propynyl-C, 3'-(5-Me-dC), 3'-(ddC), 5-Br-dC, 5-I-dC, 5-Me-dC, 5-F-dC, carboxy-dT, convertible dA, convertible dC, convertible dG, convertible dT, convertible dU, 7-deaza-dG, 8-Br-dG, 8-oxo-dG, $O^6$-Me-dG, S6-DNP-dG, 4-methyl-indole, 5-nitroindole, 2'-OMe-inosine, 2'-dI, $O^6$-phenyl-dI, 4-methyl-indole, 2'-deoxynebularine, 5-nitroindole, 2-aminopurine, dP(purine analogue), dK(pyrimidine analogue), 3-nitropyrrole, 2-thio-dT, 4-thio-dT, biotin-dT, carboxy-dT, $O^4$-Me-dT, $O^4$-triazol dT, 2'-OMe-propynyl-U, 5-Br-dU, 2'-dU, 5-F-dU, 5-I-dU, $O^4$-triazol dU.

Further modifications of polynucleotides include hapten- or protein-labeling. Haptens include e.g. biotin and digoxigenin whereas proteins include enzymes such as soybean or horseradish peroxidase, β-galactosidase, luciferase, alkaline phosphatase, glutathione S-transferase or dihydrofolate reductase or may constitute heterologous epitopes such as (histidine)$_6$-tag, protein A, maltose-binding protein, Tag•100 epitope (EETARFQPGYRS; SEQ ID NO:22), c-myc epitope (EQKLISEEDL; SEQ ID NO:23), FLAG®-epitope (DYKD-DDK; SEQ ID NO:24), lacZ, CMP (calmodulin-binding peptide), HA epitope (YPYDVPDYA; SEQ ID NO:25), protein C epitope (EDQVDPRLIDGK; SEQ ID NO:26) and VSV epitope (YTDIEMNRLGK; SEQ ID NO:27). Other proteins include histones, single-strand binding protein (ssB) and native and engineered fluorescent proteins such as green-, red-, blue-, yellow-, cyan-fluorescent proteins. Crosslinking moieties can also be incorporated such as coumarins, furocoumarins or benzodipyrones, or derivates of any thereof.

In a further embodiment said terms "polynucleotide", "polynucleic acid", "nucleic acid sequence", "nucleotide sequence", "nucleic acid molecule", "oligonucleotide", "probe" or "primer" also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors. PNA probes can generally be shorter than DNA probes and are generally from 6 to 20 bases in length and more optimally from 12 to 18 bases in length (Nielsen, 2001).

In a further embodiment said terms further encompass locked nucleic acids (LNAs) which are RNA derivatives in which the ribose ring is constrained by a methylene linkage between the 2'-oxygen and the 4'-carbon. LNAs display unprecedented binding affinity towards DNA or RNA target sequences. LNA nucleotides can be oligomerized and can be incorporated in chimeric or mix-meric LNA/DNA or LNA/RNA molecules. LNAs seem to be nontoxic for cultured cells (Orum et al., 2001; Wahlestedt et al., 2000). In general, chimeras or mix-mers of any of DNA, RNA, PNA and LNA are considered as well as any of these wherein thymine is replaced by uracil.

The term "nucleic acid polymorphism" or "nucleotide sequence polymorphism" is meant to include any difference in the primary nucleotide sequence of the nucleic acid under investigation relative to the primary nucleotide sequence of one or more reference nucleic acids. The most simple nucleic acid polymorphism is a polymorphism affecting a single nucleotide, i.e. a single nucleotide polymorphism or SNP. Nucleic acid polymorphisms further include any number of contiguous and/or non-contiguous differences in the primary nucleotide sequence of the nucleic acid under investigation relative to the primary nucleotide sequence of one or more reference nucleic acids. The above explanation also clarifies terms like "polymorphic variant".

An assessment of a potential viral variant is important for the selection of an appropriate therapeutic protocol. Such an assessment is suitably facilitated with the assistance of a computer programmed with software. Thus, in yet another embodiment, said isolated HBV polynucleic acid sequences or fragments thereof, or the amino acid sequences derived thereof, may be in ASCII-, hexadecimal- or UNICODE code, in a single-byte, double-byte or multiple-byte character set or in a binary code. In an additional embodiment, said sequences in ASCII-, hexadecimal- or UNICODE code, in a single-, double- or multi-byte character set or in binary code are readable by a computer. In a further embodiment, said sequences in ASCII-, hexadecimal- or UNICODE code, in a single-, double- or multi-byte character set or in binary code are recordable on a computer readable carrier or are incorporatable in a computer-readable database. In yet another embodiment is covered computer readable carriers comprising said sequences in ASCII-, hexadecimal- or UNICODE code, in a single-, double- or multi-byte character set or in binary code. In yet another further embodiment of the invention is envisaged a computer readable database comprising said sequences in ASCII-, hexadecimal- or UNICODE code, in a single-, double- or multi-byte character set or in binary code. In yet another further embodiment, said sequences in ASCII-, hexadecimal- or UNICODE code, in a single-, double- or multi-byte character set or in binary code is used in algorithms capable of comparing sequences or capable of aligning sequences.

In a further aspect of the present invention is comprised a vector comprising the isolated HBV polynucleic acid or fragment thereof according to the invention. In a specific embodiment, said vector is an expression vector. In another specific embodiment, said vector is a viral or a retroviral vector.

In a further embodiment, said vector is a universal cloning vector such as the pUC-series or pEMBL-series vectors or cloning vectors such as cloning vectors requiring a DNA topoisomerase reaction for cloning, TA-cloning vectors and recombination-based cloning vectors such as those used in the Gateway system (InVitrogen). Vectors comprise plasmids, phagemids, cosmids or bacmids (baculovirus vectors). A vector can merely function as a cloning tool and/or -vehicle or may additionally comprise regulatory sequences such as promoters, enhancers and terminators or polyadenylation signals. Said regulatory sequences may enable expression of the information contained within the DNA fragment of interest cloned into a vector comprising said regulatory sequences. Expression may be the production of RNA molecules or mRNA molecules and, optionally, the production of protein molecules thereof. Expression may be the production of an RNA molecule by means of a viral polymerase promoter (e.g. SP6, T7 or T3 promoter) introduced to the 5'- or 3'-end of the DNA of interest.

Expression may furthermore be transient expression or stable expression or, alternatively, controllable expression. Controllable expression comprises inducible expression, e.g. using a tetracyclin-regulatable promoter, a stress-inducible (e.g. human hsp70 gene promoter), a methallothionine promoter, a glucocorticoid promoter or a progesterone promoter. Promoters further include HBV promoters such as the core promoter and heterologous promoters such as the cytomegalovirus (CMV) immediate early (IE) promoter.

A promoter can also preferably drive expression in liver tumour cells, e.g. the promoter and enhancer of the α-foetoprotein gene. Expression vectors are known in the art that mediate expression in bacteria (e.g. *Escherichia coli*, *Streptomyces* species), fungi (e.g. *Saccharomyces cerevisiae*, *Schizosaccharomyces pombe*, *Pichia pastoris*, *Aspergillus* species, *Hansenula polymorpha*, *Neurospora crassa*), insect cells (*Spodoptera frugiperda* cells, Sf9 cells), plant cells (e.g. potato virus X-based expression vectors, see e.g. Vance et al. 1998 in International Patent Publication No WO 98/44097) and mammalian cells (e.g. CHO or COS cells, Vero cells, cells from the HeLa cell line). Particularly suited host cells in the context of the present invention are mammalian, e.g. human, primary hepatocytes, hepatoma cell lines (e.g. HepG2, HepT1, HepT3, Huh6, Huh7), Chang liver cells, rodent liver cells, primate liver cells, hominoid liver cells, or any other mammalian, e.g. human, host cells or cell line.

A vector, or an expression vector, may furthermore be capable of autonomous replication in a host cell or may be an integrative vector, i.e. a vector completely or partially, and stably, integrating in the genome of a host cell. Integration of any first DNA fragment, e.g. a vector or a fragment thereof, in any other second DNA fragment, e.g. the genome of a host cell, can be reversed if said first DNA fragment is flanked e.g. by site-specific recombination sites or by repeat sequences typical for transposons. Alternatively, said site-specific recombination sites or transposon-repeat sequences are comprised in said second DNA fragment and are flanking said first DNA fragment. In yet another alternative, said first DNA fragment can possibly be introduced in a thereto suitable second DNA fragment by homologous recombination and the same process can be used to exchange said first DNA fragment with another thereto suitable DNA fragment.

Introduction of a vector, or an expression vector, into a host cell may be effectuated by any available transformation or transfection technique applicable to said host cell as known in the art. Such transformation or transfection techniques comprise heat-shock mediated transformation (e.g. of *E. coli*), conjugative DNA transfer, electroporation, PEG-mediated DNA uptake, liposome-mediated DNA uptake, lipofection, calcium-phosphate DNA coprecipitation, DEAE-dextran mediated transfection, direct introduction by e.g. microinjection or particle bombardment, or introduction by means of a virus, virion or viral particle.

Infection of e.g. HepG2 cell cultures by HBV viruses (e.g. derived from a patient's serum or from a cell culture) is normally not occurring but may be stimulated by pretreatment of the host cells with dimethylsulfoxide (DMSO; (Paran et al., 2001)). Alternatively, digestion of HBV with V8 protease results in infectious HBV viruses (Lu et al., 1996). A similar protease modification of at least one other hepadnavirus, woodchuck hepatitis virus (WHV), likewise results in WHV viruses which are infectious for human hepatoblastoma cells (Lu et al., 2001). Expression of HBV genes in hepatoblastoma cells was reported to increase significantly by lowering the incubation temperature from 37° C. to 32° C. (Kosovsky et al., 2000).

Vectors suited for assaying viral replication efficiency, more particularly for assaying HBV replication efficiency, include viral vectors or vectors comprising at least 1 unit (full-length) HBV genome, preferably greater than 1 unit HBV genome, e.g. 1.1-4, in particular 1.1, 1.2, 1.28, 1.3, 1.4, 1.5, 1.6, 1.7, 1.8, 1.9, 2.0, 3.0 or 4.0 times the HBV genome. One example of a viral vector system enabling HBV viral replication is a baculoviral system, e.g. as described by Isom and Harriet in International Patent Publication No WO99/37821 or by Delaney et al. (Delaney et al., 1999). The extent of viral replication can be monitored by measuring or detecting either one or more of (i) secrection of an HBV antigen (HBsAg or HBeAg), (ii) expression of HBV transcripts (3.5 kb-, 2.4 kb-, 2.1 kb-, 0.7 kb-transcripts), (iii) the amount of HBV replicative intermediates (relaxed circular DNA, double stranded DNA or single stranded DNA), (iv) the amount of HBV supercoiled circular (ccc) DNA, (v) the amount of secreted extracellular HBV DNA, (vi) the amount of extracellularly produced HBV particles, (vii) the amount of produced HBcAg protein, (viii) the amount of produced HBV DNA polymerase/reverse transcriptase protein, and (ix) the amount of produced HBV X protein. Another example of a viral vector system enabling HBV viral replication is a vector system which includes an indicator gene (e.g. a selectable marker gene or a screenable marker gene; e.g. as described by Capon and Petropoulos in U.S. Pat. No. 6,242,187), the expression of which is indicative for the extent of viral replication.

Viral vector systems enabling HBV viral replication are suited to compare replication efficiency of wild-type HBV viruses with replication efficiency of mutant HBV viruses. Mutant HBV viruses are understood to be HBV viruses comprising a mutation or a polynucleic acid polymorphism in either one or more of the HBV ORFs and/or the HBV regulatory sequences (e.g. promoter, enhancer, terminator or polyadenylation signal, epsilon-loop, encapsidation signal, repeat sequence, packaging signal, internal ribosome entry site).

A further aspect of the invention relates to a host cell comprising an HBV polynucleic acid or fragment thereof according to the invention, or comprising an HBV DNA polymerase/reverse transcriptase protein or fragment thereof according to the invention, or comprising an HBV variant according to the invention, or comprising a vector according to the invention. In a specific embodiment, said host cell is a mammalian liver cell or a mammalian hepatoma cell as described supra.

The present invention further relates to expression products from the isolated polynucleic acids. These expression products result from the expression of any of the polynucleic acids and/or fragments described supra.

Said expression products comprise proteins, peptides, oligopeptides, RNA or mRNA. The terms "protein", "peptide" or "oligopeptide", when used herein refer to amino acids in a polymeric form of any length. Said terms also include known amino acid modifications such as disulfide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.) and acylation as well as non-naturally occurring amino acid residues, L-amino acid residues and D-amino acid residues. A number of said amino acid modifications can occur as a result of post-translational modification as will be recognized by the one skilled in the art. Other modifications include the addition of a chemical group to one or more amino acids of a protein, peptide or oligopeptide. Said chemical groups include e.g. biotin. Proteins, peptides or oligopeptides can furthermore generally be labeled radioactively, chemiluminescently, fluorescently, phosphorescently, with infrared dyes or with a surface-enhanced Raman label or plasmon resonant particle.

The present invention extends to expression products that comprise at least one amino acid substitution and/or deletion in the polymerase gene. In particular the invention relates to expression products comprising an amino acid substitution at codon 233 of the polymerase gene of an isoleucine to any other amino acid. More in particular the expression product comprises the amino acid substitution from isoleucine to valine, rtI233V.

The present invention also covers expression products that comprise besides rtI233V further amino acid substitutions of the polymerase. More preferably, the substitution of the Methionine at codon position 204 in domain C of the polymerase. In particular covered are expression products that comprise at least two amino acid substitutions in the DNA polymerase, one substitution of the isoleucine into valine at codon position 233 in domain D of the polymerase gene and one substitution of the methionine at codon position 204 in domain C of the polymerase gene. The substitution of the methionine at codon position 204 is meant to include any amino acid other than methionine, preferably the substitution is into an isoleucine or a valine or a serine.

The present invention also covers expression products that comprise besides rtI233V further amino acid substitutions at other sites of the HBV polymerase, preferably one or more amino acid substitutions chosen from the group consisting of rtV173L, rtM204I or rtM204V or rtM204S, rt S219A, rtL180M, rtA181V, L217R and rtN236T. The different mutations at codon 204 has been indicated by twice "or".

Exemplary expression products comprise the rtI233V substitution in domain B of the polymerase optionally with the rtM204I substitution in domain C of the polymerase. In a specific embodiment, said isolated HBV expression products comprise a sequence chosen from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20.

Another aspect of the invention relates to fragments of the above-mentioned expression products, which fragments comprise the described amino acid substitutions leading to a reduced sensitivity to a nucleoside analog and/or other anti-HBV agents. These fragments comprise at least the rtI233V substitution.

The expression products comprise polypeptides that include full length hepatitis B polymerase and/or reverse transcriptase and fragments thereof comprising at least the mutant residue or site, and/or either of these fused to a heterologous polypeptide.

Expression includes the production of RNA molecules or mRNA molecules comprising the disclosed mutated genotypic patterns. "Heterologous" when used in reference to polynucleic acid or protein sequences does not mean the same as native or known flanking sequences. Heterologous sequences include other HBV, human animal or microbial sequences, polyHis or other affinity tags, or entirely fabricated sequences. Fragments typically will include the variant residue plus at least about 4 total flanking residues apportioned to either or both flanks of the mutant residue, usually 10 to 20 residues in total.

The present invention further embraces the aspect of oligonucleotides capable of discriminating, in an HBV polynucleic acid or fragment thereof according to the invention, a valine-encoding codon 233 in the HBV reverse transcriptase domain from a codon 233 encoding an isoleucine in the HBV reverse transcriptase domain.

The term "oligonucleotide" as referred to herein is meant to be a primer or a probe and may be single-stranded or double-stranded or may be part of a triplex-forming polynucleic acid. Oligonucleotides can be made in vitro by means of a nucleotide sequence amplification method. If such an amplified oligonucleotide is double-stranded, conversion to a single-stranded molecule can be achieved by a suitable exonuclease given that the desired single-stranded oligonucleotide is protected against said exonuclease activity. Alternatively, oligonucleotides are derived from recombinant plasmids containing inserts including the corresponding nucleotide sequences, if need be by cleaving the latter out from the cloned plasmids upon using the adequate nucleases and recovering them, e.g. by fractionation according to molecular weight. The oligonucleotides according to the present invention can also be synthetic, i.e. be synthesized chemically, for instance by applying the conventional phospho-triester or phosphoramidite chemistry. Oligonucleotides can further be synthesized in situ on a glass slide via solid-phase oligonucleotide synthesis or via photolitographic synthesis (Beaucage, 2001).

In another specific embodiment, the oligonucleotide according to the present invention further comprises a modification for attaching said oligonucleotide to a solid support. Said modification may for instance be an amine-, thiol-, 3-'propanolamine or Acrydite-modification of the oligonucleotide or may comprise the addition of a homopolymeric tail (e.g. an oligo(dT)-tail added enzymatically via a terminal transferase enzyme or added synthetically) to the oligonucleotide. If said homopolymeric tail is positioned at the 3'-terminus of the oligonucleotide or if any other 3'-terminal modification preventing enzymatic extension is incorporated in the oligonucleotide, the priming capacity of the oligonucleotide can be decreased or abolished. Other modifications are described in e.g. (Beaucage, 2001). Clearly, oligonucleotides according to the present invention which are DNA, RNA, PNA or LNA, or which are any chimaera thereof are embodied in the invention. Further embodied are compositions comprising at least one oligonucleotide according to the invention.

"Hybridization" is the process wherein substantially homologous complementary nucleotide sequences anneal to each other. The hybridization process can occur entirely in solution, i.e. both complementary nucleic acids are in solution. Tools in molecular biology relying on such a process include PCR, subtractive hybridization and DNA sequence determination. The hybridization process can also occur with one of the complementary nucleic acids immobilized to a matrix such as magnetic beads, Sepharose beads or any other resin or type of beads. Tools in molecular biology relying on such a process include the isolation of poly (A$^+$) mRNA. The hybridization process can furthermore occur with one of the complementary nucleic acids immobilized to a solid support such as a nitrocellulose or nylon membrane, a glass slide or fused silica (quartz) slide (the latter known as nucleic acid arrays or microarrays or as nucleic acid chips), a gold film, a polypyrrole film, an optical fiber or in e.g. a polyacrylamide gel or a microplate well. Tools in molecular biology relying on such a process include RNA and DNA gel blot analysis, colony hybridization, plaque hybridization, reverse hybridization and microarray hybridization. In order to allow hybridization to occur, the nucleic acid molecules are generally thermally, chemically (e.g. by NaOH) or electrochemically denatured to melt a double strand into two single strands and/or to remove hairpins or 'Molecular Beacons' probes (single dual-labeled) or other secondary structures from single stranded nucleic acids.

The nucleic acid sequences of the invention may furthermore be linked to an external guide sequence (EGS) or a short external guide sequence (SEGS). Said guide sequences linked to a target sequence provide a minimal structure that is recognized as a substrate by RNAse P enzymes (Werner and George in U.S. Pat. No. 5,877,162). Nucleic acid sequences of the invention linked to an EGS or a SEGS may find therapeutic applications in treating HBV-infected patients.

Further aspects of the present invention are methods for detecting the presence of an HBV virus in a biological sample; and/or for detecting resistance to an antiviral drug of an HBV virus present in a biological sample; and/or for detecting the presence of a valine-encoding codon 233, optionally together with the presence of one or more codons chosen from the group consisting of a leucine encoding codon 173, an isoleucine-encoding codon 204 or a valine-encoding codon 204 or a serine-encoding codon 204, an alanine encoding codon 219, a methionine-encoding codon 180, a valine encoding codon 181, an arginine encoding codon 217 and a threonine-encoding codon 236 in the HBV reverse transcriptase domain an HBV virus present in a biological sample.

With "codon" is meant a combination of 3 contiguous nucleotides that encode an amino acid according to the genetic code. A "codon" in the present invention furthermore can be comprised in a single-stranded (sense or antisense) or double-stranded (poly)nucleic acid. For deriving the amino acid sequence from an antisense strand, the corresponding sense strand (the inverted complement) needs to be used for translation into the corresponding amino acid sequence.

A large number of assays capable of detecting nucleotide sequences and nucleotide sequence polymorphisms (e.g. a mutation) is currently available. Some of these assays are based on physical methods whereas others use enzymatic approaches.

With "physical detection methods" is meant in the present context methods of nucleotide sequence polymorphism detection that require one or more physical processes for detection although not excluding the enzymatic process of prior PCR amplification of the target DNA sequence comprising one or more nucleotide sequence polymorphisms. Said physical processes include electrophoresis, chromatography, spectrometry, optical signal sensing and spectroscopy.

Physical nucleotide sequence polymorphism detection assays include electrophoretic methods such as single stranded conformation polymorphism (SSCP), constant denaturant capillary electrophoresis (CDCE) and constant denaturant gel electrophoresis (CDGE) see for instance Kristensen et al., 2001; denaturing gradient gel electrophoresis (DGGE), double gradient capillary electrophoresis (DGCE), capillary zone electrophoresis (CZE) is also known as free-solution capillary electrophoresis (FSCE), nonisocratic CZE, or thermal gradient capillary electrophoresis (TGCE), two-dimensional gene scanning (TDGS), conformation sensitive gel electrophoresis (CSGE), see for instance Korkko et al., 1998, microplate-array diagonal gel electrophoresis (MADGE), see for instance Day et al., 1998 and double-strand conformation analysis (DSCA), see for instance (Arguello et al., 1998). A similar technique is called HMA (heteroduplex mobility assay) but detection of DNA-duplexes relies on in gel staining of the DNA (Delwart et al., 1993). In HTA (heteroduplex tracking assay), a radiolabeled probe is annealed to a PCR product and the probe-PCR product heteroduplexes are separated by gel electrophoresis. A multiple-site-specific HTA has been described (Resch et al., 2001; Delwart et al., 1994).

Double-strand conformation analysis chromatographic methods include denaturing high-performance liquid chromatography (DHPLC). Physical nucleotide sequence polymorphism detection assays may be effective for identification of known or new mutations and may require confirmation by direct DNA sequencing resulting in separation of homo- and heteroduplex target DNA molecules by denaturing electrophoresis. Said separation can also be performed by denaturing liquid chromatography wherein temperature determines sensitivity. DHPLC can moreover be performed in monolithic capillary columns enabling the setting up of an array system. Fluorescence-based detection is possible, as well as on-line coupling to a mass spectrometer. The efficiency of nucleotide polymorphism detection by DHPLC can be increased by adding a GC-clamp to the end of the target DNA fragment (Huber et al., 2001; Narayanaswami et al., 2001; Xiao et al., 2001).

MALDI-TOF MS (matrix-assisted laser desorption-ionization time-of-flight mass spectrometry) has been successfully used both as a direct DNA sequencing tool for DNA fragments under 100 bp and as a tool for detection of single nucleotide polymorphisms. Hybridization of allele-specific PNA-oligomers (peptide nucleic acid) with single stranded target DNA was proven to be highly compatible with MALDI-TOF MS analysis ((Griffin et al., 2000), and references therein).

Still regarded as the 'gold standard' for determination of nucleotide sequence polymorphisms is direct DNA sequencing as for instance designed by Maxam and Gilbert (Maxam et al., 1977). The most common and widespread DNA sequencing method is based on the Sanger reaction or dideoxynucleotide chain termination reaction (Sanger et al., 1977). Sequencing primers can be labeled for detection of the terminated chains or internal labeling of the extension product is possible. Other DNA sequencing methods are pyrosequencing (see e.g. Williams 2000) and cycle sequencing (Yager et al., 1999; Ruano et al., 1991).

In the near future, nanopore sequencing might also become available (Meller et al., 2000). Other DNA sequencing methods include molecular resonance sequencing and diagnostic sequencing by combining specific cleavage of DNA followed by mass spectrometric analysis of the fragments (see e.g. Stanssens and Zabeau 2000—WO00/66771).

Another method of determining nucleotide sequence variations comprises dideoxynucleotide sequencing (Sanger reaction) wherein the regular dNTPs are replaced by modified dNTPs (such as α-thio dNTPs) and other variants (Dahlhauser 2000—U.S. Pat. No. 6,150,105).

Yet another DNA sequencing methodology is known as SBH or sequencing-by-hybridization which uses an array of all possible n-nucleotide oligomers (n-mers) to identify n-mers comprised in an unknown DNA sample (Drmanac et al., 1993).

Said high-density oligonucleotide arrays or DNA chips abolish the need to design a set of oligonucleotides specifically hybridizing under the same conditions to a set of polymorphic nucleotide sequences. The latter approach is applied in conventional reverse blot assays by carefully adjusting length, polarity and position of the mismatched nucleotide(s) in the oligonucleotide probe (Saiki et al., 1989). Conventional reverse blot hybridization assays for genotyping and detection of nucleotide sequence polymorphisms have, however, been successfully commercialized, e.g. in the LiPA (Line Probe Assay) format (Innogenetics, Ghent, Belgium). (Stuyver et al., 1997; Stuyver et al., 1996).

It will be clear to the skilled artisan that many variations and combinations can be made to the nucleotide sequence and nucleotide sequence polymorphism detection methods described supra. These are hereby incorporated in the present invention.

The oligonucleotides according to the invention as described supra can be adapted such that they can be used in any of the methods for detection of nucleotide sequences or polymorphisms therein as described supra.

Thus, in an additional embodiment of the present invention, the oligonucleotide according to the invention further comprises a terminal extension and/or a hairpin or 'Molecular Beacons' probe structure, wherein said extension and/or hairpin structure is incorporated at either end or at both ends of said oligonucleotide. Said terminal extension is useful for, e.g., specifically hybridizing with another nucleic acid molecule, and/or for facilitating attachment of said oligonucleotide to a solid support, and/or for modification of said tailed oligonucleotide by an enzyme, ribozyme or DNAzyme.

In a further embodiment of the current invention, the oligonucleotide according to the invention is comprised within a padlock probe that incorporates at either end primers which, after annealing to a target DNA, can be ligated, or within a hairpin structure.

In another embodiment, the oligonucleotide of the present invention has a modification allowing detection and/or capturing of said oligonucleotide. Detection and/or capturing of said oligonucleotide furthermore enables detection and/or capturing of the target nucleic acid hybridized therewith. The interaction between said oligonucleotide and said target nucleic acid may be stabilized by cross-linking both via introduction of a cross-linking modification in said oligonucleotide and/or said target nucleic acid.

In yet another embodiment, the oligonucleotide of the invention comprises a 3'-terminal mismatching nucleotide and, optionally, a 3'-proximal mismatching nucleotide. Said oligonucleotides are particularly useful for performing polymorphism-specific PCR and LCR (Ligase Chain Reaction) or GAP-LCR.

Further comprised in the present invention is a composition comprising at least one oligonucleotide according to the description given supra.

It will be clear to the skilled artisan that any of the methods described supra for detecting nucleotide sequences and polymorphisms therein can be utilized for methods for detecting the presence of an HBV virus in a biological sample; and/or for detecting the presence of a valine-encoding codon 233, optionally together with the presence of one or more codons chosen from the group consisting of a leucine encoding codon 173, an isoleucine-encoding codon 204 or a valine-encoding codon 204 or a serine-encoding codon 204, an alanine encoding codon 219, a methionine-encoding codon 180, a valine encoding codon 181, an arginine encoding codon 217 and a threonine encoding codon 236 of the HBV reverse transcriptase domain of an HBV virus present in a biological sample.

Therefore, the following aspects covering such detection methods and diagnostic kits, e.g. line probe assays, based on such detection methods are additionally included in the present invention.

One aspect of the invention relates to a method for detecting the presence of an HBV virus in a biological sample and/or a method for detecting resistance to an antiviral drug of an HBV virus present in a biological sample, said methods comprising the step of detecting the presence of an HBV polynucleic acid or fragment thereof according to the invention. A specific embodiment thereto includes said method comprising the steps of:

a. obtaining a target HBV polynucleic acid from said biological sample wherein said target HBV polynucleic acid is suspected to comprise a valine-encoding codon 233 of the HBV reverse transcriptase domain, and optionally one or more of the codons chosen from the group consisting of a leucine-encoding codon 173, an isoleucine-encoding codon 204 or a valine-encoding codon 204 or a serine-encoding codon 204, an alanine encoding codon 219, a methionine-encoding codon 180, a valine encoding codon 181, an arginine encoding codon 217 and a threonine encoding codon 236 of the HBV reverse transcriptase domain of an HBV virus;

b. obtaining the nucleic acid sequence of the target HBV polynucleic acid of (a);

c. infering, from the nucleic acid sequence obtained in (b), the presence of said valine encoding codon 233 of the HBV reverse transcriptase domain, and optionally one or more codons chosen from the group mentioned in (a)

and, therefrom, the presence of said HBV virus in said biological sample and/or said resistance to an antiviral drug of an HBV virus present in said biological sample.

Another specific embodiment thereto includes said methods comprising:

a. obtaining a target HBV polynucleic acid present in said biological sample and/or obtaining the nucleotide sequence thereof;

b. when appropriate, partially or completely denaturating, or enzymatically modifying the polynucleic acids obtained in step (a);

c. when appropriate, renaturating the denatured polynucleic acids obtained in step (b), preferably in the presence of at least one oligonucleotide capable of discriminating, in an HBV polynucleic acid or a fragment thereof a valine-encoding codon 233 in the HBV reverse transcriptase domain from a codon 233 encoding an isoleucine in the HBV reverse transcriptase domain, and, if needed, including the step of enzymatically modifying, including extending, said oligonucleotide;

d. when appropriate, detection of the partially or completely denatured HBV polynucleic acids obtained in step (b), and/or of the hybrids formed in step (c), and/or of the modifications obtained in step (b) and/or (c);

e. infering from one or more of the data of the following groups: the partially or completely denatured polynucleic acids, the hybrids, the enzymatic modifications, all detected in step (d), and from the nucleotide sequence obtained in (a), the presence of said HBV in said biological sample and/or said resistance to an antiviral drug of an HBV present in said biological sample.

In yet another specific embodiment thereto, said method comprising:

a. obtaining a target HBV polynucleic acid from said biological sample wherein said target HBV polynucleic acid is suspected to comprise a valine-encoding codon 233 of the HBV reverse transcriptase domain, and optionally together with one or more of the codons chosen from the group consisting of a leucine-encoding codon 173, an isoleucine-encoding codon 204 or a valine-encoding codon 204 or a serine-encoding codon 204, an alanine encoding codon 219, a methionine-encoding codon 180, a valine encoding codon 181, an arginine encoding codon 217 and a threonine encoding codon 236 of the HBV reverse transcriptase domain of an HBV;

b. contacting the target HBV polynucleic acid of (a) with an oligonucleotide capable of discriminating a codon 233 encoding a isoleucine from a codon 233 encoding an alanine or valine, and optionally also capable of discriminating one or more codons chosen from the group consisting of a codon 173 encoding a valine from a codon 173 encoding a leucine, a codon 204 encoding a methionine from a codon 204 encoding a protein chosen from the group consisting of isoleucine, valine and serine, a codon 219 encoding a serine from a codon 219 encoding an alanine, a codon 180 encoding a leucine from a codon 180 encoding a methionine, a codon 181 encoding a alanine from a codon 181 encoding a valine, a codon 217 encoding a leucine from a codon 217 encoding a arginine and a codon 236 encoding an asparagine from a codon 236 encoding a threonine;

c. infering, from the discriminatory signal obtained in (b), the presence of said valine encoding codon 233 of the HBV reverse transcriptase, optionally together with said leucine-encoding codon 173 or said alanine encoding codon 219 or said methionine-encoding codon 180, or said valine-encoding codon 181 or said isoleucine-encoding codon 204 or said valine-encoding codon 204 or said serine-encoding codon 204, or said arginine encoding codon 217 or said threonine encoding codon 236 of the HBV reverse transcriptase domain of an HBV;

and, therefrom, the presence of said HBV in said biological sample and/or said resistance to an antiviral drug of an HBV virus present in said biological sample.

In the latter methods, said discriminating in (b) is generally based on hybridization and said discriminatory signal in (c) is a hybridization signal.

With an "oligonucleotide capable of discriminating, in a (poly)nucleic acid, a codon encoding amino acid X1 (any amino acid) from a codon encoding amino acid X2 (any amino acid different from X1)" is meant an oligonucleotide yielding a signal when contacted with a (poly)nucleic acid comprising said codon encoding amino acid X1 but not yielding a signal when contacted with a (poly)nucleic acid comprising a codon encoding amino acid X2. Said signal, also referred to as "discriminatory signal", may be any signal obtainable by using said oligonucleotide in any of the assays capable of detecting nucleotide sequences and nucleotide sequence polymorphisms as described supra. Said signals include, e.g., fluorescent signals, (chemi) luminescent signals, radioactive signals, light signals, hybridization signals, mass spectrometric signals, spectrometric signals, chromatographic signals, electric signals, electronic signals, electrophoretic signals, real-time PCR signals, PCR signals, LCR signals, CFLP-assay signals and Invader-assay signals.

With "contacting an oligonucleotide with a (poly)nucleic acid" or vice versa is generally meant annealing of said oligonucleotide with said (poly)nucleic acid or hybridizing said oligonucleotide with said (poly)nucleic acid. "Contacting an oligonucleotide with a (poly)nucleic acid" does not exclude and can thus further comprise enzymatic modification of said oligonucleotide wherein said modification may occur at the extremities of said oligonucleotide and/or internally in the nucleotide sequence of said oligonucleotide. Examples of enzymatic modifications of oligonucleotides are given in, e.g., the assays capable of detecting nucleotide sequences and nucleotide sequence polymorphisms described herein.

In another embodiment of the invention said methods further comprise, where applicable, aligning and/or comparing the obtained nucleic acid sequence with a set of HBV nucleic acid sequences contained within a database.

With "database" is meant in the present context a collection of nucleic acid or amino acid sequences, more specifically of HBV nucleic acid or amino acid sequences. A database is to be understood to comprise at least one nucleic acid or at least one amino acid sequence. A database can be recorded on a variety of carriers. Such carriers include computer readable carriers.

Another aspect of the current invention relates to a diagnostic kit for detecting the presence of an HBV virus in a biological sample and/or for detecting resistance to an antiviral drug of an HBV virus present in a biological sample, said kit comprising at least a means for detecting the presence of an HBV polynucleic acid according to the invention.

Preferably said diagnostic kit comprises:

a. a means for infering, from the nucleic acid sequence of a target polynucleic acid suspected to comprise a valine-encoding codon 233 of the HBV reverse transcriptase domain, optionally together with one or more of the codons chosen from the group consisting of a leucine-encoding codon 173, a codon 204 encoding a methionine from a codon 204 encoding a protein chosen from the group consisting of isoleucine, valine and serine, an alanine encoding codon 219, a methionine-encoding codon 180, a valine encoding codon 181, an arginine encoding codon 217 and a threonine encoding codon 236 of the HBV reverse transcriptase domain;

the presence of said valine-encoding codon 233 of the HBV reverse transcriptase domain optionally together with one or more codons from the group consisting of said leucine-encoding codon 173, said isoleucine-encoding codon 204 or said valine-encoding codon 204 or said serine-encoding codon 204, said alanine encoding codon 219, said methionine-encoding codon 180, said valine encoding codon 181, an arginine encoding codon 217 and a threonine encoding codon 236 of the HBV reverse transcriptase domain; and, therefrom, the presence in said biological sample of said HBV and optionally, b. a means for obtaining the nucleic acid sequence of the target polynucleic acid.

In another embodiment, said diagnostic kit additionally comprises a means for detecting the discriminatory signal obtained by contacting said HBV polynucleic acid with said oligonucleotide or oligonucleotides.

Furthermore embodied are said diagnostic kits wherein said oligonucleotide or oligonucleotides are attached or immobilized to a solid support.

Another specific embodiment thereto includes said diagnostic kits comprising:

a. a means for obtaining a target HBV polynucleic acid present in said biological sample and/or obtaining the nucleotide sequence thereof;
b. when appropriate, at least one oligonucleotide pair suitable for amplification of a target HBV polynucleic acid according to the invention;
c. when appropriate, a means for denaturing nucleic acids;
d. when appropriate, at least one oligonucleotide according to the invention;
e. when appropriate, an enzyme capable of modifying a double stranded or single stranded nucleic acid molecule;
f. when appropriate, a hybridization buffer, or components necessary for producing said buffer;
g. when appropriate, a wash solution, or components necessary for producing said solution;
h. when appropriate, a means for detecting partially or completely denatured polynucleic acids and/or a means for detecting hybrids formed in the preceding hybridization and/or a means for detecting enzymatic modifications of nucleic acids;
i. when appropriate, a means for attaching an oligonucleotide to a known location on a solid support;
j. a means for infering from the partially or completely denatured polynucleic acids and/or from the hybrids and/or from the enzymatic modifications, all detected in (h), and/or from the nucleotide sequence obtained in (a), the presence of said HBV virus in said biological sample.

With "a means for infering, from a nucleic acid sequence, the presence of codon Y (Y is number as indicated) encoding amino acid X (X is amino acid as indicated)" is meant any technique or method to (i) localize in said nucleic acid sequence said codon Y, (ii) to translate said codon Y into the amino acid encoded by codon Y, and (iii) to conclude from (ii) if the amino acid encoded by said codon Y is the same as or is different from said amino acid X. Said means can include methods wherein (i) to (iii) all are performed manually and/or computationally. Said means may include aligning and/or comparing an obtained nucleic acid sequence with a set of nucleic acid sequences contained within a database. Said means may furthermore include the result of (i) to (iii) being presented in the form of a report wherein said report can be in paper form, in electronic form or on a computer readable carrier or medium. Said means may furthermore include the searching of (nucleic acid and/or amino acid) sequence databases and/or the creation of (nucleic acid and/or amino acid) sequence alignments, the results of which may or may not be included in said report.

A further embodiment covers any of the above methods of the invention characterized further in that said methods are based on determining the nucleic acid sequence.

A further embodiment covers any of the above methods of the invention characterized further in that said methods are based on a hybridization assay.

A further embodiment covers any of the above methods of the invention characterized further in that said methods are based on a reverse hybridization assay.

A further embodiment covers any of the above diagnostic kits of the invention characterized further in that said diagnostic kits are based on determining the nucleic acid sequence.

A further embodiment covers any of the above diagnostic kits of the invention characterized further in that said diagnostic kits are based on a hybridization assay.

A further embodiment covers any of the above diagnostic kits of the invention characterized further in that said diagnostic kits are based on a reverse hybridization assay.

A further embodiment covers any of the above diagnostic kits of the invention characterized further in that said diagnostic kits are based on a line probe assay.

The invention further provides a method for detecting resistance to an antiviral drug of an HBV virus present in a biological sample, said method comprising the step of detecting the presence of an HBV DNA polymerase/reverse transcriptase protein or fragment according to the invention. Said detection may include the steps of determining the amino acid sequence of the HBV DNA polymerase/reverse transcriptase protein or from a part thereof obtained, e.g., after proteolytic digestion and separation of the resulting protein fragments via chromatographic and/or electrophoretic means. After electrophoresis, a protein fragment may be excised and eventually eluted from the gel before sequencing. Alternatively, the protein gel electrophoresis is combined with blotting whereby proteins are transferred to a membrane carrier (e.g. nitrocellulose, PVDF, nylon). The protein or protein fragment to be sequenced can in the latter case be excised from the membrane carrier. Alternatively, the HBV DNA polymerase/transcriptase protein according to the invention is detected using an antibody specifically recognizing the valine at position 233 of the HBV reverse transcriptase domain. In particular, said antibody should not recognize an isoleucine at said position 233. In yet another alternative, the HBV DNA polymerase/reverse transcriptase according to the invention is detected phenotypically, i.e. said HBV DNA polymerase/transcriptase may display a unique pattern of antiviral drug sensitivity not shared with HBV DNA polymerase/reverse transcriptases comprising a codon 233 encoding an isoleucine.

Phenotypic detection of the HBV DNA polymerase/reverse transcriptase according to the invention thus includes e.g. the steps of determining the sensitivity of an activity of an HBV DNA polymerase/reverse transcriptase from an HBV virus present in a biological sample to a panel of antiviral drugs. Alternatively, the HBV DNA polymerase/reverse transcriptase from an HBV virus present in a biological sample and suspected to comprise a polynucleic acid according to the invention is produced in a recombinant system and the sensitivity to a panel of antiviral drugs is determined of an activity of the recombinantly expressed HBV DNA polymerase/reverse transcriptase.

It will be clear to the person skilled in the art that a vector system enabling HBV viral replication or enabling production of an HBV-encoded protein, or a functional part thereof, is suited for testing or assaying the effect of an antiviral drug on the HBV viral replication or function of the HBV-encoded protein (or part thereof), respectively. In particular, such assays can be performed with a mutant HBV polynucleic acid according to the present invention or with a mutant HBV DNA polymerase or mutant HBsAg protein according to the present invention. The results of such assays can be compared to results of similar assays performed with wild-type HBV polynucleic acids or wild-type HBV proteins, or functional parts thereof.

A person skilled in the art will appreciate that the HBV DNA polymerase/reverse transcriptase has multiple recognized biological/biochemical functions including primase activity, reverse transcriptase activity (RNA-dependent DNA polymerase activity), DNA polymerase activity (DNA-dependent DNA polymerase activity) and RNAse (RNAse H) activity and is furthermore involved in the interaction with the core antigen protein (HBcAg) and in the encapsidation of the viral DNA. Wild-type or mutant HBV DNA polymerase can be isolated from HBV particles present in a patient's serum or can be produced by e.g. a stably transformed hepatoma cell line. Alternatively, said HBV DNA polymerase is expressed and produced in a heterologous system (e.g. S. cerevisiae) or by using a baculovirus expression system, a mitochondrial translation system (e.g. as described in U.S. Pat. No. 6,100, 068) or in a cell-free system, e.g. a rabbit reticulocyte lysate coupled transcription-translation system (Li et al., 1999). Mutant HBV DNA polymerase DNA sequences can be produced by in vitro mutagenesis. Substantial purification of produced HBV DNA polymerase/reverse transcriptase can be achieved if e.g. a heterologous epitope (e.g. the FLAG epitope, cfr supra) is introduced in or fused to said HBV DNA polymerase/reverse transcriptase. Said epitope allows purification of the HBV DNA polymerase/reverse transcriptase e.g. on an affinity column containing immobilized anti-heterologous epitope antibodies (e.g. anti-FLAG M2 monoclonal antibodies). Alternatively, the recombinant HBV polymerase/reverse transcriptase is part of fusion protein, said fusion protein further comprising e.g. a histidine-tag, a carbohydrate-binding moiety (e.g. lectin, maltose binding protein) or β-galactosidase. Substantial purification of said fusion protein is achievable by e.g. metal-affinity chromatography (in case a histidine-tag is present), carbohydrate-affinity chromatography (in case a carbohydrate-binding moiety is present) or immuno-affinity chromatography using an antibody against the protein fused to the HBV DNA polymerase/ reverse transcriptase, e.g. β-galactosidase. Optionally, said fusion protein is cleavable by a suitable protease (e.g. protease factor Xa) such that the HBV DNA polymerase/reverse transcriptase is obtainable separated from the other moiety of the fusion protein, e.g. by another round of purification as described supra. Alternatively, HBV viral particles are isolated from a biological sample by techniques such as affinity capture (e.g. using antibodies against the HBV viral surface antigen or using a protein receptor to said surface antigen or anti-idiotypic antibodies to said protein receptor, cfr. infra) or gradient centrifugation. HBV viral particles obtainable via these or other ways are further amenable to analysis e.g. of the HBV DNA polymerase/reverse transcriptase or of the HBV nucleic acids.

In yet another alternative, the multiprotein replicating core complex or intracellular replicating core are purified from infected liver cells and the obtained preparations comprising the HBV DNA polymerase/reverse transcriptase are used to assay the functions and activities of the HBV DNA polymerase/reverse transcriptase (Urban et al., 2000). Clearly, said purification of viral particles or of the replicating core complex can be applied to obtain said particles or core complex from cells infected with HBV variants comprising the mutation or mutations of the present invention.

Improved conditions for assaying viral reverse transcriptase activity have been described (Bird and Chang-Yeh in U.S. Pat. No. 5,817,457) and include acidic pH and elevated temperatures. Reaction conditions for assaying activity of RNAse H derived from the HBV DNA polymerase/reverse transcriptase have been described by e.g. Yoon et al. in U.S. Pat. No 6,071,734. Assay conditions to determine primase-, polymerase-, and reverse transcriptase activity of in vitro produced HBV DNA polymerase/reverse transcriptase, or fragments thereof, have been described by Li et al. (Li et al., 1999). Assays to determine protein-protein interaction, e.g. interaction between the HBV DNA polymerase/reverse transciptase and HBcAg, include two- and three-hybrid assays and real-time biomolecular interaction analysis (BIA). (Bartel et al., 1997 and U.S. Pat. No. 5,928, 868).

Another additional aspect of the invention comprises an assay determining the effect of an antiviral drug on the function of a mutant HBsAg according to the present invention. A person skilled in the art will appreciate that the HBV HBsAg has multiple recognized biological/biochemical functions including functions in viral attachment/entry into the host cell (i.e. a role in infectivity of HBV), in viral particle assembly and in the secretion of viral particles. HBsAg is furthermore a target of the host's immune system and 'escape' mutants have been reported. The antibody against HBsAg, HBIg, is often used as a passive immunization means in patients that have undergone a liver transplant. Wild-type or mutant HBsAg can be obtained as described supra for HBV DNA polymerase. Alternatively, HBsAg is recovered by affinity interaction with antibodies against HBsAg or with an HBsAg receptor protein or with an anti-idiotypic antibody to said HBsAg receptor protein, said reported receptor proteins including monomeric and polymeric human albumin (Eibl et al. in U.S. Pat. No. 5,576,175 and Machida et al., 1984, respectively) and endonexinII/annexinV (Yap in European Patent No EP 0672136). HBV and HDV (hepatitis delta virus) viral particles may be isolated from a biological sample by techniques such as affinity capture e.g. using antibodies against the HBV viral surface antigen or using a receptor to the HBV viral surface antigen or anti-idiotypic antibodies thereto.

In an alternative aspect of the invention, activity of an HBV DNA polymerase/reverse transcriptase, including the mutant HBV DNA polymerase/reverse transcriptases of the invention, or the sensitivity thereof to antiviral compounds is assayed in host cells containing a conditional mutation in the endogenous DNA polymerase. As such, expression of the HBV DNA polymerase/reverse transcriptase can possibly rescue growth of said mutant host cells under restrictive conditions. Sensitivity of the HBV DNA polymerase/reverse transcriptase to antiviral compounds can be assayed by measuring the extent of growth of said mutant host cells under restrictive conditions and in the presence of an antiviral compound. Said growth is subsequently compared to growth of said host cells under restrictive conditions and in the absence of said antiviral compound.

In a further alternative aspect of the invention is included the use of mutant HBV particles, including HBV particles comprising a mutant DNA according to the present invention, to infect non-human animals which are useful as a model for human HBV infection or as a model for evaluating anti-HBV compounds, therapies and prohylaxes. Said model non-human animals have been described, e.g. by Reisner in U.S. Pat. Nos. 5,849,987 and 5,858,328. Many antiviral drugs against HBV (HBV antiviral drugs) are mentioned above. A further aspect of the invention thus includes a method for screening for drugs active against an HBV virus comprising a polynucleic acid according to the invention or comprising an HBV DNA polymerase/reverse transcriptase according to the invention, said method comprising:
a. measuring replication of said HBV in the absence of said drug;
b. measuring replication of said HBV in the presence of said drug;
c. inferring from (a) and (b) the inhibitory effect of said drug on replication of said HBV.

In a specific embodiment thereto, said method further comprises performing steps (a), (b) and (c) with a wild-type HBV virus and comparing the inhibitory effect of said drug on replication of said wild-type HBV virus with the inhibitory effect of said drug on replication of said HBV virus comprising a polynucleic acid according to the invention. In yet another further embodiment thereto are included said methods further comprising obtaining said HBV virus from a biological sample.

Yet another further embodiment of the invention includes a method for screening for drugs active against an HBV virus comprising a polynucleic acid according to the invention or comprising an HBV DNA polymerase/reverse transcriptase according to the invention, said method comprising:
a. measuring a DNA polymerase/reverse transcriptase activity of said HBV virus in the absence of said drug;
b. measuring the same DNA polymerase/reverse transcriptase activity as in (a) of said HBV virus in the presence of said drug;
c. inferring from (a) and (b) the inhibitory effect of said drug on said DNA polymerase/reverse transcriptase activity of said HBV virus.

In a specific embodiment thereto is included said method further comprising performing steps (a), (b) and (c) with a wild-type HBV virus and comparing the inhibitory effect of said drug on a DNA polymerase/reverse transcriptase activity of said wild-type HBV virus with the inhibitory effect of said drug on said DNA polymerase/reverse transcriptase activity of said HBV virus comprising a polynucleic acid according to the invention. In yet another further specific embodiment thereto are included said methods further comprising obtaining said HBV virus from a biological sample. With "a DNA polymerase/reverse transcriptase activity" is meant either one of the biological or biochemical activities of the HBV DNA polymerase/reverse transcriptase as mentioned supra.

In a particular embodiment thereto three HBV-monoinfected patients (indicated with 1, 2 and 3) infected with lamivudine resistant HBV strains displayed no virologic reaction on adefovir; a therapy switch to tenofovir resulted in a significant drop of HB-viral load. HBV-DNA was isolated and the DNA-polymerase gene was amplified by PCR for sequencing. Sequencing was carried out using the BigDye terminator reaction. Genotyping and lamivudine-resistance testing were carried out with the INNO-LiPA assay or by sequencing of PCR products as further elaborated in the examples.

Adefovir was useless in all three patients. Sequencing analysis of all HBV strains analysed from the three patients revealed no amino acid exchange at the Adefovir-resistance positions or rt181, rt 217 or rt 236. These HBV patients were infected with HBV genotype D, accompanied by the unusual pattern HBsAg subtype ayw4, i.e. amino acid sP/T127I, which is very rare in Central Europe. Said HBV patients displayed all three a unique mutation, rtI233V (see FIG. 3).

Recently three HBV/HIV coinfected patients were described by us which did not respond to adefovir virologically within 6 months of treatment with respect to HBV load (Schildgen et al., 2004). In these cases of the HIV-infected patients we identified mutations in a nonconserved HBV polymerase-region (aa rt217) that might mediate adefovir resistance. In these cases the HBV had genotype A. In the 3 mono-infected cases described in the present patent application, the HBV genotype was D and remarkably all three patients had a virus with a rtI233V mutation. The significance of this exchange is not yet known, but the mutation rtN236T has been observed nearby in a case in which resistance to adefovir developed (Angus et al., 2003). In contrast, the rtV233I exchange seen in our patients existed even before adefovir therapy and was obviously independent of the lamivudine resistance mutations. The three adefovir-resistant cases on which we previously reported (Schildgen et al., 2004) had an L217R mutation before adefovir therapy. Patient 1 had a S219A mutation nearby, but patients 2 and 3 were wt in that region (see FIG. 3).

Another previously observed mutation associated with adefovir resistance is A181V (Yang et al., 2003) but our patients did not show mutations in that region.

Possibly, some HBV strains are primarily resistant to adefovir without any selective pressure by the drug. The existence of the rt233V mutation is independent of lamivudine resistance, because in the HBV of patient 1 no such mutation was present at the beginning of adefovir therapy but the viremia immediately began to increase upon treatment. Furthermore, the HBeAg or immune status does not seem to be important for adefovir resistance, because they were different in all 3 patients. The rapid and strong effect of tenofovir in all three patients suggests that noncompliance was not the reason for the failure of the adefovir therapy.

Based on our data we draw the conclusions, that (a) the polymerase/reverse-transcriptase domain aa 215 to aa 236 might mediate adefovir resistance, (b) the combination of the lamivudine resistance plus HBV, especially in case of genotypes A or D, predestinates resistance to Adefovir, and (c) a therapy change to tenofovir should be considered indeed in the case of adefovir resistant HBV strains.

The invention further embodies antibodies and anti-idiotypic antibodies against said isolated HBV variants and/or said isolated HBV small viral surface antigen, or said parts thereof, and/or said HBV middle and/or large viral antigens. In a specific embodiment thereto, said antibodies are monoclonal antibodies. In a further specific embodiment, said antibodies are humanized monoclonal antibodies.

Further embodied in the invention is the use of said antibodies in immunological methods for detecting said HBV variants and/or said HBV small viral surface antigen, or said parts thereof, and/or said HBV middle and/or large viral antigens in a biological sample. In a specific embodiment thereto, said antibodies are used in a method for diagnosing HBV infection. In a further embodiment, said antibodies are part of a diagnostic kit capable of detecting HBV infection.

In another embodiment of the invention is covered the use of a method of the invention or a diagnostic kit of the invention to follow progression of HBV infection.

A further embodiment covers the use of a method of the invention or a diagnostic kit of the invention to monitor the occurrence of resistance to an antiviral drug.

Another further embodiment covers the use of a method of the invention or a diagnostic kit of the invention to adapt a therapeutic regimen against HBV, infection due to the occurrence of resistance to an antiviral drug.

"Antibodies" include monoclonal, polyclonal, synthetic or heavy chain camel antibodies as well as fragments of antibodies such as Fab, Fv or scFv fragments. Monoclonal antibodies can be prepared by the techniques as described in e.g. Liddle et al. (Liddle et al., 1991) which comprise the fusion of mouse myeloma cells to spleen cells derived from immunized animals. Furthermore, antibodies or fragments thereof to a molecule or fragments thereof can be obtained by using methods as described in e.g. Harlow et al. (Harlow et al., 1988). In the case of antibodies directed against small peptides such as fragments of a protein of the invention, said peptides are generally coupled to a carrier protein before immunization of animals. Such protein carriers include keyhole limpet hemocyanin (KLH), bovine serum albumin (BSA), ovalbumin and Tetanus toxoid. The carrier protein enhances the immune response of the animal and provides epitopes for T-cell receptor binding sites. The term "antibodies" furthermore includes derivatives thereof such as labelled antibodies. Antibodies can generally be labeled radioactively, chemiluminescently, fluorescently, phosphorescently, with infrared dyes or with a surface-enhanced Raman label or plasmon resonant particle. Antibody labels include alkaline phosphatase, PKH2, PKH26, PKH67, fluorescein (FITC), Hoecst 33258, R-phycoerythrin (PE), rhodamine (TRITC), Quantum Red, Texas Red, Cy3, biotin, agarose, peroxidase and gold spheres. Tools in molecular biology relying on antibodies against a protein include protein gel blot analysis, screening of expression libraries allowing gene identification, protein quantitative methods including ELISA (enzyme-linked immunosorbent assay), RIA (radio-immuno-assay) and LIA (line immuno-assay), immunoaffinity purification of proteins, immunoprecipitation of proteins and immunolocalization of proteins.

The following examples only serve to illustrate the present invention. These examples are in no way intended to limit the scope of the present invention.

EXAMPLES

Materials and Methods: Isolation and Sequencing of HBV DNA

HBV-DNA was isolated from serum with the Viral DNA kit (Qiagen) according to the manufacturers instruction. The DNA-polymerase gene was amplified by PCR for sequencing. The protocol used was adopted from Allen et al. 1998. Primers used for the amplification were P1F (GGA TGT GTC TGC GGC GTT T, SEQ ID 28) and P1R (ACC CCA TCT TTT TGT TTT GTT AGG, SEQ ID 29). The PCR was carried out with the Qiagen-HotStar Taq polymerase using the reagents supplied by the manufacturer and the following temperature profile: 93° C., 12 min, 95° C., 30 sec, 65° C., 45 sec, 72° C., 3 min, 45× 95° C., 30 sec, 60° C., 45 sec, 72° C., 3 min, 95° C., 30 sec, 55° C., 45 sec, 72° C., 3 min, 72° C., 10 min.

Sequencing was carried out using the BigDye terminator reaction (Applied Biosystems) with primers P1F and P1R, respectively. Genotyping and lamivudine-resistance testing were carried out with the INNO-LiPA assay (Innogenetics) following the included protocol.

Alternatively, the HBV DNA was extracted from serum and amplified in the RT region as described (Schaefer et al., 2003) using sense primer 374-390 TGGATGTGTCT-GCGGC, SEQ ID 30 and antisense primer 995-973 CKT-TGACADACTTTCCAATCAATAG, SEQ ID 31. The gel-purified PCR products were sequenced by MWG Biotech, Ebersberg, Germany in both directions. Alternatively, sequencing was done as described by Schildgen et al (2004).

Example 1

Case Study patient 1

Patient 1, a 52 year old Caucasian male, had suffered for over 5 years from chronic hepatitis B. He had received an unsuccessful therapy with PegIntron and thereafter an initially effective therapy with 100 mg/d LMV which suppressed viremia to levels <200 genomes/ml. However, within three months viremia increased to $2.5 \times 10^7$ g/ml (see FIG. 1). After an interval without therapy, 100 mg/d of the RT inhibitor and licensed HIV medication tenofovir (TDF) was administered as an experimental drug against hepatitis B virus for 9 months and viremia decreased within 3 months from $5.5 \times 10^7$ ge/ml to 740 ge/ml and remained at similar levels for another 6 months. The lamivudine resistance mutation in the reverse transcriptase domain from methionine 204 to isoleucine rtM204V had already reverted to wildtype (wt) before the tenofovir therapy (see FIG. 3). Thereafter, TDF was replaced by 10 mg/d of the RT inhibitor ADF because this drug had meanwhile been licensed for therapy of chronic hepatitis B. However, under this therapy viremia increased immediately from 550 ge/ml and within 7 months reached $1.5 \times 10^6$ ge/ml. Replacement of ADF by TDF resulted again in a significant decrease of viremia to 17,000 ge/ml. The patient had normal or slightly elevated ALT levels. He was anti-HBe positive with a normal precore sequence but with core promoter mutations T1753C, A1762T and G1764A, which are known to be associated with HBeAg negativity.

Example 2

Case Studies of Patients 2 and 3

Patients 2 and 3 are a married couple. The husband, a 56 year old Caucasian male had received a liver transplant in 1993 because of alcoholic liver disease and became HBV-infected during follow-up. He was under constant immune suppression. His wife (Caucasian, 52 years, patient 3) was found to be chronically HBV infected in 1994. The genome sequences of their HBVs were very similar but he had a precore-negative mutant with the stop codon mutant G1896A as the predominant variant whereas she had only the wild-type, however, both were HBeAg positive. Both received lamivudine and their viremia dropped initially from $>10^7$ g/ml to levels $<10^5$ g/ml, but finally resistance developed and viremia again increased (see FIG. 1). Both had the lamivudine resistance-associated mutation rtM204I and she had furthermore rtV173L (see FIG. 3). Lamivudine was replaced by adefovir, but it was not effective. With patient 2 viremia increased under therapy, with patient 3 it remained very high. Tenofovir led to a rapid decrease from $>5 \times 10^8$ g/ml to 780 g/ml for patient 2 and from $4.5 \times 10^7$ to 29,000 g/ml for patient 3.

Example 3

Effect of Antiviral Therapy and Nucleotide Sequences

After about 18 month of lamivudine therapy, the viral load increased due to lamivudine resistance mutations (rtM204I for patients 2 and 3). Therefore adefovir was introduced into the drug regimen. Surprisingly, although none of the mutations hitherto known or supposed to mediate adefovir resistance: rtA181V (Yang et al., 2003), rtN236T (Angus et al., 2003); rtL217R (Schildgen et al., 2004), see supra, was observed, the patients did not show even an initial response to this drug. Instead a common mutation at the codon position 233 (I⇒V), that may mediate the drug resistance was identified. The initial nonresponse to adefovir may be caused by the fact, that the mutation was already present when the adefovir therapy started (FIG. 3).

Example 4

In Vitro Testing and Confirmation of rtI233V Mediated Adefovir Resistance

To determine whether the rtI223V exchange alone is necessary and sufficient to mediate resistance of HBV to adefovir, the isoleucine 233 of the plasmid vector pTHBV1.3 for wildtype (wt) HBV genotype D (Guidotti et al., 1995) was mutated to valine by site-directed mutagenesis using the primer pair sense 5'-CTT TTG TCT TTG GGT gTA CAT TTA AAC CCT AAC-3' (SEQ ID NO 32) and antisense 5'-GTT AGG GTT TAA ATG TAc ACC CAA AGA CAA AAG-3 (SEQ ID NO 33). Successful introduction of the mutation was confirmed by sequencing. The HepG2 subclonal cell line C3A (from ATCC, Rockville USA) growing in 6-well cell culture plates at a density of 50% was transfected with 12 µg of wt or mutated plasmid. On the next day, the cells were passaged into 12-well cell culture plates. To eliminate input DNA, cells were treated with 100 µg/mL DNAse I (Roche) at 37° C. for 2 h.

Two days after transfection cells were treated with adefovir, tenofovir (Moravek, Brea, Calif.), or lamivudine at concentrations ranging from 0.1 µM to 10 µM. Medium supplemented with the drugs was renewed daily. Cell culture supernatants and cells were harvested on day 6. Replicative intermediates of HBV DNA were extracted as described by Summers et al., (1990) subjected to Southern blotting (Rang et al., 2002) and hybridized with a $P^{32}$-labelled probe generated with the Ready Prime Labelling System (Amersham UK) from a full-length HBV DNA fragment. The quantity of HBV DNA was significantly decreased in the treated cells (FIG. 4). With the wt, 50% inhibition was obtained at ca. 0.5 µM adefovir which is slightly higher than described by Yang et al. (2002) but lower than the findings of Brunelle et al. (2005). The rt233I variant required ca 6 fold higher concentrations of adefovir for a similar inhibition. This exceeds variations which have previously been described between naturally occurring strains (Yang et al. (2002)). In contrast, the efficacy of tenofovir and lamivudine was not significantly different with the wt or the variant. Lamivudine was by far the most efficaceous drug in this in vitro system.

The cell culture medium was digested with proteinase K and subjected to PCR using the following subgenomic primers: F1 5'-CTC CAG TTC AGG AAC AGT AAA CCC-3' (SEQ ID NO 34) and the corresponding reverse primer R1 5'-TTG TGA GCT CAG AAA GGC CTT GTA AGT TGG CG-3' (SEQ ID NO 35). Serial dilutions of a cloned HBV genome served for calibration of the PCR assay. Amplified products were analysed on an ethidium bromide stained agarose gel (FIG. 5) and quantified using the Fluor-S MultiImager (Biorad) and Quantity One software (data not shown). The amount of released wt HBV DNA was strongly decreased by ca 80% at 1 µM adefovir whereas the amount of the variant decreased only by 10%. In this assay, the variant required about a 10 fold higher adefovir concentration than the wt for the same degree of inhibition. These in vitro data suggest that the exchange of I to V at position rt 233 caused the adefovir resistance in vivo.

The rtI233V exchange already existed before adefovir therapy was initiated. It was independent of lamivudine resistance since in patient 1 no lamivudine resistance mutation was present at the beginning of adefovir therapy. Neither HBe status nor the immune status seem to be important for adefovir resistance, since they were different in the 3 patients. Furthermore, the variant rt233V was stable during the observation period of the three patients (i.e. up to 220 weeks) even without selective pressure from adefovir therapy.

REFERENCES

Allen M I, Deslauriers M, Andrews C W, Tipples G A, Walters K A, Tyrrell D L J et al. Identification and characterization of mutations in hepatitis B virus resistant to lamivudine; (1998) Hepatology 27(6), 1670-1677.

Angus P. et al. Resistance to adefovir dipivoxil therapy associated with the selection of a novel mutation in the HBV polymerase. *Gastroenterology* (2003) 125(2): 292-297.

Arguello, J. R., Little, A. M., Pay, A. L., Gallardo, D., Rojas, I., Marsh, S. G., Goldman, J. M. & Madrigal, J. A. (1998) Nat Genet 18, 192-194

Bartel, P. L. & Fields, S. (1997) The yeast two-hybrid system. Oxford University Press, Beaucage, S. L. (2001) Curr Med Chem 8, 1213-1244

Benhamou Y. et al. Antiretroviral therapy and HIV/hepatitis B virus coinfection. *Clin. Infect. Dis.* (2004) 38 Suppl 2:S98-103.

Benhamou Y. et al. Safety and efficacy of adefovir dipivoxil in patients co-infected with HIV-1 and lamivudine-resistant hepatitis B virus: an open-label pilot study. *Lancet* (2001) 358: 718-723.

Benhamou Y. et al. Tenofovir disoproxil fumarate in patients with HIV and lamivudine-resistant hepatitis B virus. *N. Engl. J. Med.* (2003) 348(2):177-178.

Brunnelle M N, Jacquard A C, Pichoud C, Durantel D, Carrouée-Durantel S, Villeneuve J P, Trépo C, Zoulim F. (2005) Susceptibility to antiviral of a human HBV strain with mutations conferring resistance to both lamivudine and adefovir. Hepatology 41, 1391-8.

Day, I. N., Spanakis, E., Palamand, D., Weavind, G. P. & O'Dell, S. D. (1998) Trends. Biotechnol. 16, 287-290

De Clercq, E. (1999) Int. J Antimicrob Agents 12, 81-95

Delaney, W. E., Miller, T. G. & Isom, H. C. (1999) Antimicrob Agents Chemother 43, 2017-2026

Delwart, E. L., Sheppard, H. W., Walker, B. D., Goudsmit, J. & Mullins, J. I. (1994) J Virol 68, 6672-6683

Delwart, E. L., Shpaer, E. G., Louwagie, J., McCutchan, F. E., Grez, M., Rubsamen-Waigmann, H. & Mullins, J. I. (1993) Science 262, 1257-1261

Dore G. J. et al. Efficacy of tenofovir disoproxil fumarate in antiretroviral therapy-naive and -experienced patients coinfected with HIV-1 and hepatitis B virus. *J. Infect. Dis.* (2004) 189(7):1185-1192.

Drmanac, R., Drmanac, S., Strezoska, Z., Paunesku, T., Labat, I., Zeremski, M., Snoddy, J., Funkhouser, W. K., Koop, B. & Hood, L. (1993) Science 260, 1649-1652

Fu, L. & Cheng, Y. C. (2000) Antimicrob Agents Chemother 44, 3402-3407

Griffin, T. J. & Smith, L. M. (2000) Trends. Biotechnol. 18, 77-84

Guidotti L G, Matzke B, Schaller H, Chisari F V (1995). High-level hepatitis B virus replication in transgenic mice. J Virol., 69, 6158-69.

Harlow, E. & Lane, D. (1988) Antibodies: A Laboratory Manual. Cold Spring Harbor Laboratory Press, Huber, C. G., Premstaller, A., Xiao, W., Oberacher, H., Bonn, G. K. & Oefner, P. J. (2001) J Biochem Biophys Methods 47, 5-19

Jarvis, B. & Faulds, D. (1999) Drugs 58, 101-141

Knodell, R. G., Ishak, K. G., Black, W. C., Chen, T. S., Craig, R., Kaplowitz, N., Kiernan, T. W. & Wollman, J. (1981) Hepatology 1, 431-435

Korkko, J., Annunen, S., Pihlajamaa, T., Prockop, D. J. & Ala-Kokko, L. (1998) Proc Natl Acad Sci USA 95, 1681-1685

Kosovsky, M. J., Khaoustov, V. I., Rushton, M. & Yoffe, B. (2000) Biochim Biophys Acta 1490, 63-73

Kristensen, V. N., Kelefiotis, D., Kristensen, T. & Borresen-Dale, A. L. (2001) Biotechniques 30, 318-22, 324, 326

Li, Z. & Tyrrell, D. L. (1999) Biochem Cell Biol 77, 119-126

Liddle, J. E. & Cryer, A. (1991) A Practical Guide to Monoclonal Antibodies. Wiley, N.Y.

Lok, A. S. (1994) J Viral. Hepat. 1, 105-124

Lu, X., Block, T. M. & Gerlich, W. H. (1996) J Virol 70, 2277-2285

Lu, X., Hazboun, T. & Block, T. (2001) Virus Res 73, 27-40

Luscombe, C. A. & Locarnini, S. (1996) Viral hepatitis reviews 2, 1-35

Machida, A., Kishimoto, S., Ohnuma, H., Baba, K., Ito, Y., Miyamoto, H., Funatsu, G., Oda, K., Usuda, S. & Togami, S. (1984) Gastroenterology 86, 910-918

Maxam, A. M. & Gilbert, W. (1977) Proc Natl Acad Sci USA 74, 560-564

Meller, A., Nivon, L., Brandin, E., Golovchenko, J. & Branton, D. (2000) Proc Natl Acad Sci USA 97, 1079-1084

Narayanaswami, G. & Taylor, P. D. (2001) Genet Test. 5, 9-16

Nielsen, P. E. (2001) Curr Med Chem 8, 545-550

Ogata N., Fujii K., Takigawa S., Nomoto M., Ichida T. & Asakura H. (1999) J. Med. Virol. 59, 270-276.

Ono, S. K., Kato, N., Shiratori, Y., Kato, J., Goto, T., Schinazi, R. F., Carrilho, F. J. & Omata, M. (2001) J Clin Invest 107, 449-455

Orum, H. & Wengel, J. (2001) Curr Opin. Mol. Ther. 3, 239-243

Paran, N., Geiger, B. & Shaul, Y. (2001) EMBO J 20, 4443-4453

Perrillo R. et al. Adefovir dipivoxil added to ongoing lamivudine in chronic hepatitis B with YMDD mutant hepatitis B virus. *Gastroenterology* (2004) 126(1):81-90.

Peters M. G. et al. Adefovir dipivoxil alone or in combination with lamivudine in patients with lamivudine-resistant chronic hepatitis B. *Gastroenterology* (2004) 126(1):91-101.

Rang A, Bruns M, Heise T, Will H. (2002) Antiviral activity of interferon-alpha against hepatitis B virus can be studied in non-hepatic cells and is independent of MxA. J Biol Chem. 277, 7645-7.

Resch, W., Parkin, N., Stuelke, E. L., Watkins, T. & Swanstrom, R. (2001) Proc Natl Acad Sci USA 98, 176-181

Ruano, G. & Kidd, K. K. (1991) Proc Natl Acad Sci USA 88, 2815-2819

Saiki, R. K., Walsh, P. S., Levenson, C. H. & Erlich, H. A. (1989) Proc Natl Acad Sci USA 86, 6230-6234

Sanger, F., Nicklen, S. & Coulson, A. R. (1977) Proc Natl Acad Sci USA 74, 5463-5467

Schaefer et al. (2003) J Clin Virol 2003 27, 30-37

Schildgen O, Schewe C K, Vogel M et al. (2004) Successful therapy of hepatitis B with tenofovir in HIV-infected patients failing previous adefovir and lamivudine treatment. AIDS 18, 2325-2327

Schinazi, R. (1997) in Viral hepatitis and liver disease (Rizzetto, M., Purcell, R., Gerin, J. & Verme, G., eds.), Impact of nucleosides on hepatitis virus. pp. 736-742, Minerva Medica, Torino Stuyver, L., De Gendt, S., Van Geyt, C., Zoulim, F., Fried, M., Schinazi, R. F. & Rossau, R. (2000) J Gen. Virol 81 Pt 1, 67-74

Stuyver, L., Wyseur, A., Rombout, A., Louwagie, J., Scarcez, T., Verhofstede, C., Rimland, D., Schinazi, R. F. & Rossau, R. (1997) Antimicrob Agents Chemother 41, 284-291

Stuyver, L., Wyseur, A., van Arnhem, W., Hernandez, F. & Maertens, G. (1996) J Clin Microbiol 34, 2259-2266

Stuyver, L. J., Locarnin, S. A., Lok, A., Richman, D. D., Carman, W. F., Dienstag, J. L. & Schinazi, R. F. (2001) Hepatology 33, 751-757

Summers J., Mason W. *Cell* (1982) 29: 403-415.

Summers J, Smith P M, Horwich A L. (1990) Hepadnavirus envelope proteins regulate covalently closed circular DNA amplification. J Virol. 64, 2819-24.

Urban, S. & Tyrrell, D. L. (2000) Antiviral Res 45, 185-197

Wahlestedt, C., Salmi, P., Good, L., Kela, J., Johnsson, T., Hokfelt, T., Broberger, C., Porreca, F., Lai, J., Ren, K., Ossipov, M., Koshkin, A., Jakobsen, N., Skouv, J., Oerum, H., Jacobsen, M. H. & Wengel, J. (2000) Proc Natl Acad Sci USA 97, 5633-5638

Westland C E et al. Week 48 resistance surveillance in two phase 3 clinical studies of adefovir dipivoxil for chronic hepatitis B. *Hepatology* (2003) 38(1): 96-103.

Xiao, W. & Oefner, P. J. (2001) Hum Mutat 17, 439-474

Yager, T. D., Baron, L., Batra, R., Bouevitch, A., Chan, D., Chan, K., Darasch, S., Gilchrist, R., Izmailov, A., Lacroix, J. M., Marchelleta, K., Renfrew, J., Rushlow, D., Steinbach, E., Ton, C., Waterhouse, P., Zaleski, H., Dunn, J. M. & Stevens, J. (1999) Electrophoresis 20, 1280-1300

Yang H. et al. Complete Genotypic and Phenotypic Analyses of HBV Mutations Identified in HBeAg-negative Chronic Hepatitis B Patients Receiving 96 Weeks of Adefovir Dipivoxil (ADV). *Hepatology* (2003) 38: 705A., C. T., Chien, R. N., Chu, C. M. & Liaw, Y. F. (2000) Hepatology 31, 1318-1326

Yang H, Westland C, Xiong S, Delaney IV W E. In vitro antiviral susceptibility of full-length clinical hepatitis B virus isolates cloned with a novel expression vector. Antivir Res. (2002) 61, 27-36.

What is claimed is:

1. A method of detecting Hepatitis B virus (HBV) variant in a biological sample, said HBV variant comprising at least one nucleotide mutation in the DNA polymerase gene at codon position 233 which results in a substitution of an isoleucine to any other amino acid, said method comprising the step of detecting the presence of a HBV polynucleic acid or a fragment of a HBV polynucleic acid in a biological sample, said HBV polynucleic acid or said fragment comprising a nucleotide mutation at codon position 233 that results in an amino acid substitution of an isoleucine of the DNA polymerase gene in the HBV variant to any other amino acid in the HBV variant, or the step of detecting the expression product of said HBV polynucleic acid or said fragment comprising said amino acid substitution.

2. The method of claim 1 wherein said mutation results in a substitution of an isoleucine to valine, I233V.

3. The method of claim 1 wherein said variant exhibits a decreased sensitivity to a nucleoside analogue, except of tenofovir.

4. The method of claim 1 wherein said variant exhibits a decreased sensitivity to the nucleoside analogue Adefovir and/or Lamivudine.

5. The method of claim 1 wherein said method further comprises assaying for one or more further nucleotide mutations in the DNA polymerase gene chosen from the group consisting of a nucleotide at codon 173, at codon 204 and at codon 219 wherein said further nucleotide mutation at codon position 173 of the polymerase gene results in the amino acid substitution of the valine to any amino acid other than valine, at codon position 204 of the polymerase gene results in the amino acid substitution of the methionine to any amino acid other than methionine, and at codon position 219 of the polymerase gene results in the amino acid substitution of the serine to any amino acid other than serine.

6. The method of claim 5 wherein said further nucleotide mutation at codon 204 results in the amino acid substitution of methionine to isoleucine, at codon 173 results in the amino acid substitution of the valine to leucine and at codon 219 results in the amino acid substitution of the serine to alanine.

7. The method of claim 1 wherein said method further comprises assaying for a further nucleotide mutation that results in an additional amino acid substitution in addition to codon position 233 of the DNA polymerase gene in the HBV variant.

8. The method of claim 7, wherein said method further comprises assaying for a further nucleotide mutation that results in a mutation at codon position 204 of the DNA polymerase gene in the variant and results in the amino acid substitution of the methionine to any amino acid other than methionine.

9. The method of claim 8, wherein said method further comprises assaying for a nucleotide mutation that results in rtI233V substitution in domain D of the DNA polymerase gene in the variant, and a nucleotide mutation that results in rtM204I substitution in domain C of the DNA polymerase gene in the variant.

10. The method of claim 7, wherein said method further comprises assaying for a polynucleic acid chosen from the group consisting of SEQ ID NO:1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

11. The method of claim 7 wherein said method further comprises assaying for a polynucleic acid encoding a polyamino acid chosen from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20.

12. A method of detecting Hepatitis B virus (HBV) variant in a biological sample, said HBV variant comprising at least one nucleotide mutation in the DNA polymerase gene at codon position 233 which results in a substitution of an isoleucine to any other amino acid, said method comprising the step of detecting the presence of a HBV polynucleic acid or a fragment of a HBV polynucleic acid in a biological sample, said HBV polynucleic acid or said fragment comprising a nucleotide mutation that results in an amino acid substitution of an isoleucine of the DNA polymerase gene in the HBV variant to any other amino acid in the HBV variant.

13. The method according to claim 12 comprising:
  a) obtaining a target HBV polynucleic acid from said biological sample wherein said target HBV polynucleic acid is suspected to comprise a valine-encoding codon 233 of the HBV reverse transcriptase domain, and optionally one or more of the codons chosen from the group consisting of a leucine-encoding codon 173, an isoleucine-encoding codon 204 or a valine-encoding codon 204 or a serine-encoding codon 204, an alanine encoding codon 219, a methionine-encoding codon 180, a valine encoding codon 181, an arginine encoding codon 217 and a threonine encoding codon 236 of the HBV reverse transcriptase domain of an HBV virus;
  b) obtaining the nucleic acid sequence of the target HBV polynucleic acid of (a);
  c) inferring, from the nucleic acid sequence obtained in (b), the presence of said valine-encoding codon 233 of the HBV reverse transcriptase domain, and optionally one or more codons chosen from the group mentioned in (a) and, therefrom, determining the presence of said HBV virus in said biological sample.

14. The method according to claim 12 further comprising:
a) obtaining a target HBV polynucleic acid present in said biological sample and/or obtaining the nucleotide sequence thereof;
b) partially or completely denaturating, or enzymatically modifying the polynucleic acids obtained in step (a);
c) optionally, renaturating the denatured polynucleic acids obtained in step (b), optionally in the presence of at least one oligonucleotide capable of discriminating, in an HBV polynucleic acid or a fragment thereof a valine-encoding codon 233 in the HBV reverse transcriptase domain from a codon 233 encoding an isoleucine in the HBV reverse transcriptase domain, and, optionally, including the step of enzymatically modifying, including extending, said oligonucleotide;
d) optionally, detection of the partially or completely denatured HBV polynucleic acids obtained in step (b), and/or of the hybrids formed in step (c), and/or of the enzymatic modifications obtained in step (b) and/or (c);
e) inferring from one or more of the data of the following groups: the partially or completely denatured polynucleic acids, the hybrids, the enzymatic modifications, all detected in step (d), and from the nucleotide sequence obtained in (a), the presence of said HBV in said biological sample.

15. The method for detecting the presence of an HBV variant according to claim 12 comprising:
a) obtaining a target HBV polynucleic acid from said biological sample wherein said target HBV polynucleic acid is suspected to comprise a valine-encoding codon 233 of the HBV reverse transcriptase domain, and optionally together with one or more of the codons chosen from the group consisting of a leucine-encoding codon 173, an isoleucine-encoding codon 204 or a valine-encoding codon 204 or a serine-encoding codon 204, an alanine encoding codon 219, a methionine-encoding codon 180, a valine encoding codon 181, an arginine encoding codon 217 and a threonine encoding codon 236 of the HBV reverse transcriptase domain of an HBV;
b) contacting the target HBV polynucleic acid of (a) with an oligonucleotide capable of discriminating a codon 233 encoding a isoleucine from a codon 233 encoding an alanine or valine, and optionally also capable of discriminating one or more codons chosen from the group consisting of a codon 173 encoding a valine from a codon 173 encoding a leucine, a codon 204 encoding a methionine from a codon 204 encoding an amino acid chosen from the group consisting of isoleucine, valine and serine, a codon 219 encoding a serine from a codon 219 encoding an alanine, a codon 180 encoding a leucine from a codon 180 encoding a methionine, a codon 181 encoding an alanine from a codon 181 encoding a valine, a codon 217 encoding a leucine from a codon 217 encoding a arginine and a codon 236 encoding an asparagine from a codon 236 encoding a threonine;
c) infering, from the discriminatory signal obtained in (b), the presence of said valine encoding codon 233 of the HBV reverse transcriptase, optionally together with said leucine-encoding codon 173 or said alanine encoding codon 219 or said methionine-encoding codon 180, or said valine-encoding codon 181 or said isoleucine-encoding codon 204 or said valine-encoding codon 204 or said serine-encoding codon 204, or said arginine encoding codon 217 or said threonine encoding codon 236 of the HBV reverse transcriptase domain of an HBV;
and, therefrom, determining the presence of said HBV in said biological sample.

16. A method for detecting a drug-resistant HBV-variant present in a biological sample, said variant being resistant to an antiviral drug, except of tenofovir, said HBV variant comprising at least one nucleotide mutation in the DNA polymerase gene at codon 233 which results in an iso-leucine to any other amino acid substitution rtI233X, said method comprising the step of detecting the presence of a HBV polynucleic acid comprising a nucleotide mutation that results in an amino acid substitution rtI233X of the DNA polymerase gene in the HBV variant, or a fragment of said HBV polynucleic acid comprising said nucleotide mutation, wherein the presence of said HBV polynucleic acid indicates resistance of an HBV virus present in said biological sample to an antiviral drug.

17. A method according to claim 16 comprising:
a) obtaining a target HBV polynucleic acid from said biological sample wherein said target HBV polynucleic acid is suspected to comprise a valine-encoding codon 233 of the HBV reverse transcriptase domain, and optionally one or more of the codons chosen from the group consisting of a leucine-encoding codon 173, an isoleucine-encoding codon 204 or a valine-encoding codon 204 or a serine-encoding codon 204, an alanine encoding codon 219, a methionine-encoding codon 180, a valine encoding codon 181, an arginine encoding codon 217 and a threonine encoding codon 236 of the HBV reverse transcriptase domain of an HBV;
b) obtaining the nucleic acid sequence of the target HBV polynucleic acid of (a);
c) infering, from the nucleic acid sequence obtained in (b), the presence of said valine-encoding codon 233 of the HBV reverse transcriptase domain, and optionally one or more codons chosen from the group mentioned in (a) and, therefrom said resistance of an HBV virus present in said biological sample to an antiviral drug.

18. The method according to claim 16 comprising:
a) obtaining a target HBV polynucleic acid from said biological sample wherein said target HBV polynucleic acid is suspected to comprise a valine-encoding codon 233 of the HBV reverse transcriptase domain, and optionally one or more of the codons chosen from the group consisting of a leucine-encoding codon 173, an isoleucine-encoding codon 204 or a valine-encoding codon 204 or a serine-encoding codon 204, an alanine encoding codon 219, a methionine-encoding codon 180, a valine encoding codon 181, an arginine encoding codon 217 and a threonine encoding codon 236 of the HBV reverse transcriptase domain of an HBV;
b) contacting the target HBV polynucleic acid of (a) with an oligonucleotide capable of discriminating a codon 233 encoding an iso-leucine from a codon 233 encoding an alanine or valine, and optionally also capable of discriminating one or more codons chosen from the group consisting of a leucine-encoding codon 173, an isoleucine-encoding codon 204 or a valine-encoding codon 204 or a serine-encoding codon 204, an alanine encoding codon 219, a methionine-encoding codon 180, a valine encoding codon 181, an arginine encoding codon 217 and a threonine encoding codon 236; and
c) infering, from the discriminatory signal obtained in (b), the presence of said valine-encoding codon 233 of the HBV reverse transcriptase, optionally together with said leucine-encoding codon 173, an isoleucine-encoding codon 204 or a valine-encoding codon 204 or a serine-encoding codon 204, an alanine encoding codon 219, a methionine-encoding codon 180, a valine encoding codon 181, an arginine encoding codon 217 and a threonine encoding codon 236 of the HBV reverse transcriptase domain and, therefrom, the resistance of an HBV virus present in said biological sample to an antiviral drug.

* * * * *

SEQUENCE LISTING

<160> NUMBER OF SEQ ID NOS: 36

<210> SEQ ID NO 1
<211> LENGTH: 465
<212> TYPE: DNA
<213> ORGANISM: Hepatitis B Virus

<400> SEQUENCE: 1

```
gcgttttatc atcttcctct tcatcctgct gctatgcctc atcttcttgt tggttcttct      60
ggactatcaa ggtatgttgc ccgtgtgtcc t cta attccaggat ctccgaccac          114
                                  Leu
                                   1 cagtacggga ccatgcagaa cctgcacgac tattgctcaa ggaacctcta tgtatccctc     174 ctgttgctgt accaaacctt cggacggaaa ttgcacctgt attcccatcc atcatcctgg     234 gctttcggaa aattcctatg ggagtgggcc tcagccccgtt tctcctggct cagtttacta     294 gtgccatttg ttcagtggtt cgtagggctt tcccccactg tttggctttc agttatatgg     354
```

| | |
|---|---|
| atgatgtggt attggggggcc aagtctgtac agcatcttga ggcccttttt accgctgtta | 414 |
| ccaatttctc tttgtctttg ggtgtacatt taaaccctaa caaaacaaaa a | 465 |

<210> SEQ ID NO 2
<211> LENGTH: 465
<212> TYPE: DNA
<213> ORGANISM: Hepatitis B Virus

<400> SEQUENCE: 2

| | |
|---|---|
| cgcaaaatag tagaaggaga agtaggacga cgatacggag tagaagaaca accaagaaga | 60 |
| cctgatagtt ccatacaacg ggcacacagg agattaaggt cctagaggct ggtggtcatg | 120 |
| ccctggtacg tcttggacgt gctgataacg agttccttgg agatacatag ggaggacaac | 180 |
| gacatggttt ggaagcctgc ctttaacgtg gacataaggg taggtagtag gacccgaaag | 240 |
| ccttttaagg ataccctcac ccggagtcgg gcaaagagga ccgagtcaaa tgatcacggt | 300 |
| aaacaagtca ccaagcatcc cgaaaggggg tgacaaaccg aaagtcaata tacctactac | 360 |
| accataaccc ccggttcaga catgtcgtag aactccggga aaaatggcga caatggttaa | 420 |
| aagaaaacag aaacccacat gtaaatttgg gattgttttg ttttt | 465 |

<210> SEQ ID NO 3
<211> LENGTH: 557
<212> TYPE: DNA
<213> ORGANISM: Hepatitis B Virus

<400> SEQUENCE: 3

| | |
|---|---|
| cggcgtttta tcatcttcct cttcatcctg ctgctatgcc tcatcttctt gttggttctt | 60 |
| ctggactatc aaggtatgtt gcccgtttgt cctctaattc caggatcttc aaccaccagc | 120 |
| acgggaccat gcagaacctg cacgactatt gctcaaggaa cctctatgta tccctcctgt | 180 |
| tgctgtacca aaccttcgga cggaaattgc acctgtattc ccatcccatc atcctgggct | 240 |
| ttcggaaaat tcctatggga gtgggcctca gcccgtttct cctggctcag tttactagtg | 300 |
| ccatttgttc agtggttcgt agggcttttcc cccactgttt ggctttcagt tatattgatg | 360 |
| atgtggtatt gggggccaag tctgtacagc atcttgagtc ccttttttacc gctgttacca | 420 |
| attttcttttt gtctttgggt gtacatttaa accctaacaa aacaaaaaga tggggttact | 480 |
| ctttaaattt catgggctat gttattggat gttatgggtc cttgccacaa gatcacatta | 540 |
| ttcagaaaat caaagaa | 557 |

<210> SEQ ID NO 4
<211> LENGTH: 557
<212> TYPE: DNA
<213> ORGANISM: Hepatitis B Virus

<400> SEQUENCE: 4

| | |
|---|---|
| gccgcaaaat agtagaagga gaagtaggac gacgatacgg agtagaagaa caaccaagaa | 60 |
| gacctgatag ttccatacaa cgggcaaaca ggagattaag gtcctagaag ttggtggtcg | 120 |
| tgccctggta cgtcttggac gtgctgataa cgagttcctt ggagatacat agggaggaca | 180 |
| acgacatggt ttggaagcct gcctttaacg tggacataag ggtagggtag taggacccga | 240 |
| aagcctttta aggatacccct cacccggagt cgggcaaaga ggaccgagtc aaatgatcac | 300 |
| ggtaaacaag tcaccaagca tcccgaaagg gggtgacaaa ccgaaagtca atataactac | 360 |
| tacaccataa ccccggttc agacatgtcg tagaactcag ggaaaaatgg cgacaatggt | 420 |
| taaaagaaaa cagaaaccca catgtaaatt tgggattgtt ttgtttttct accccaatga | 480 |

-continued

```
gaaatttaaa gtacccgata caataaccta caatacccag gaacggtgtt ctagtgtaat    540
aagtctttta gtttctt                                                    557

<210> SEQ ID NO 5
<211> LENGTH: 557
<212> TYPE: DNA
<213> ORGANISM: Hepatitis B Virus

<400> SEQUENCE: 5
cggcgtttta tcatcttcct cttcatcctg ctgctatgcc tcatcttctt gttggttctt     60
ctggactatc aaggtatgtt gcccgtttgt cctctaattc caggatcttc aaccaccagc    120
acgggaccat gcagaacctg cacgactatt gctcaaggaa cctctatgta tccctcctgt    180
tgctgtacca aaccttcgga cggaaattgc acctgtattc ccatcccatc atcctgggct    240
ttcggaaaat tcctatggga gtgggcctca gcccgtttct cctggctcag tttactagtg    300
ccatttgttc agtggttcgt agggctttcc cccactgttt ggctttcagt tatatggatg    360
atgtggtatt gggggccaag tctgtacagc atcttgagtc ccttttttacc gctgttacca    420 attttctttt gtctttgggt gtacatttaa accctaacaa aacaaaaaga tggggttact    480
ctttaaattt catgggctat gttattggat gttatgggtc cttgccacaa gatcacatta    540
ttcagaaaat caaagaa                                                   557

<210> SEQ ID NO 6
<211> LENGTH: 557
<212> TYPE: DNA
<213> ORGANISM: Hepatitis B Virus

<400> SEQUENCE: 6
gccgcaaaat agtagaagga gaagtaggac gacgatacgg agtagaagaa caaccaagaa     60
gacctgatag ttccatacaa cgggcaaaca ggagattaag gtcctagaag ttggtggtcg    120
tgccctggta cgtcttggac gtgctgataa cgagttcctt ggagatacat agggaggaca    180
acgacatggt ttggaagcct gcctttaacg tggacataag ggtagggtag taggacccga    240
aagcctttta aggatacccct cacccggagt cgggcaaaga ggaccgagtc aaatgatcac    300
ggtaaacaag tcaccaagca tcccgaaagg gggtgacaaa ccgaaagtca atatacctac    360
tacaccataa cccccggttc agacatgtcg tagaactcag ggaaaaatgg cgacaatggt    420
taaaagaaaa cagaaaccca catgtaaatt tgggattgtt ttgttttttct accccaatga    480 gaaatttaaa gtacccgata caataaccta caatacccag gaacggtgtt ctagtgtaat    540
aagtctttta gtttctt                                                    557

<210> SEQ ID NO 7
<211> LENGTH: 478
<212> TYPE: DNA
<213> ORGANISM: Hepatitis B Virus
<220> FEATURE:
<221> NAME/KEY: misc_feature
<222> LOCATION: (468)..(477)
<223> OTHER INFORMATION: n=any
<220> FEATURE:
<221> NAME/KEY: misc_feature
<222> LOCATION: (458)..(458)
<223> OTHER INFORMATION: n=any
<220> FEATURE:
<221> NAME/KEY: misc_feature
<222> LOCATION: (14)..(15)
<223> OTHER INFORMATION: n=any
```

```
<400> SEQUENCE: 7
atatattctc ttcnncctgc tgctatgcct catcttcttg ttggttcttc tggactatca    60
aggtatgttg cccgtttgtc ctctaattcc aggatcttca accaccagca cgggaccatg   120
cagaacctgc acgactattg ctcaaggaac ctctatgtat cccttctgtt gctgtaccaa   180
accttcggac ggaaattgca cctgtattcc catcccatca tcctgggctt tcggaaaatt   240
cctatgggac tgggcctcag cccgtttctc ctggctcagt ttactagtgc catttgttca   300
gtggttcgta gggctttccc ccactgtttg gctttcagtt atattgatga tgtggtattg   360
ggggccaagt ctgtacagca tcttgagtcc cttttttaccg ctgttaccaa ttttcttttg   420
tctttgggtg tacatttaaa ccctaacaaa acaaaagnat gggggtannn nnnnnnnt    478

<210> SEQ ID NO 8
<211> LENGTH: 478
<212> TYPE: DNA
<213> ORGANISM: Hepatitis B Virus
<220> FEATURE:
<221> NAME/KEY: misc_feature
<222> LOCATION: (14)..(15)
<223> OTHER INFORMATION: n=any
<220> FEATURE:
<221> NAME/KEY: misc_feature
<222> LOCATION: (458)..(458)
<223> OTHER INFORMATION: n=any
<220> FEATURE:
<221> NAME/KEY: misc_feature
<222> LOCATION: (468)..(477)
<223> OTHER INFORMATION: n=any

<400> SEQUENCE: 8
tatataagag aagnnggacg acgatacgga gtagaagaac aaccaagaag acctgatagt    60
tccatacaac gggcaaacag gagattaagg tcctagaagt tggtggtcgt gccctggtac   120
gtcttggacg tgctgataac gagttccttg gagatacata gggaagacaa cgacatggtt   180
tggaagcctg cctttaacgt ggacataagg gtagggtagt aggacccgaa agccttttaa   240 ggatacccctg acccggagtc gggcaaagag gaccgagtca aatgatcacg gtaaacaagt   300
caccaagcat cccgaaaggg ggtgacaaac cgaaagtcaa tataactact acaccataac   360
ccccggttca gacatgtcgt agaactcagg gaaaaatggc gacaatggtt aaaagaaaac   420
agaaacccac atgtaaattt gggattgttt tgttttcnta cccccatnnn nnnnnna    478

<210> SEQ ID NO 9
<211> LENGTH: 460
<212> TYPE: DNA
<213> ORGANISM: Hepatitis B Virus
<220> FEATURE:
<221> NAME/KEY: misc_feature
<222> LOCATION: (14)..(15)
<223> OTHER INFORMATION: n=any
<220> FEATURE:
<221> NAME/KEY: misc_feature
<222> LOCATION: (458)..(458)
<223> OTHER INFORMATION: n=any

<400> SEQUENCE: 9
atatattctc ttcnncctgc tgctatgcct catcttcttg ttggttcttc tggactatca    60
aggtatgttg cccgtttgtc ctctaattcc aggatcttca accaccagca cgggaccatg   120
cagaacctgc acgactattg ctcaaggaac ctctatgtat cccttctgtt gctgtaccaa   180
accttcggac ggaaattgca cctgtattcc catcccatca tcctgggctt tcggaaaatt   240
cctatgggag tgggcctcag cccgtttctc ctggctcagt ttactagtgc catttgttca   300
```

```
gtggttcgta gggctttccc ccactgtttg gctttcagtt atattgatga tgtggtattg    360
ggggccaagt ctgtacagca tcttgagtcc ctttttaccg ctgttaccaa ttttcttttg    420
tctttgggtg tacatttaaa ccctaacaaa acaaaagnat                          460
```

<210> SEQ ID NO 10
<211> LENGTH: 460
<212> TYPE: DNA
<213> ORGANISM: Hepatitis B Virus
<220> FEATURE:
<221> NAME/KEY: misc_feature
<222> LOCATION: (14)..(15)
<223> OTHER INFORMATION: n=any
<220> FEATURE:
<221> NAME/KEY: misc_feature
<222> LOCATION: (458)..(458)
<223> OTHER INFORMATION: n=any

<400> SEQUENCE: 10

```
tatataagag aagnnggacg acgatacgga gtagaagaac aaccaagaag acctgatagt     60
tccatacaac gggcaaacag gagattaagg tcctagaagt tggtggtcgt gccctggtac    120
gtcttggacg tgctgataac gagttccttg gagatacata gggaagacaa cgacatggtt    180
tggaagcctg cctttaacgt ggacataagg gtagggtagt aggacccgaa agccttttaa    240
ggataccctc acccggagtc gggcaaagag gaccgagtca aatgatcacg gtaaacaagt    300
caccaagcat cccgaaaggg ggtgacaaac cgaaagtcaa tataactact acaccataac    360
ccccggttca gacatgtcgt agaactcagg gaaaaatggc gacaatggtt aaaagaaaac    420
agaaacccac atgtaaattt gggattgttt tgttttcnta                          460
```

<210> SEQ ID NO 11
<211> LENGTH: 30
<212> TYPE: PRT
<213> ORGANISM: Hepatitis B Virus

<400> SEQUENCE: 11

```
Val Leu Ser Ser Ser Ser Ser Cys Cys Tyr Ala Ser Ser Ser Cys
1               5                   10                  15

Trp Phe Phe Trp Thr Ile Lys Val Cys Cys Pro Cys Val Leu
            20                  25                  30
```

<210> SEQ ID NO 12
<211> LENGTH: 185
<212> TYPE: PRT
<213> ORGANISM: Hepatitis B Virus

<400> SEQUENCE: 12

```
Ala Phe Tyr His Leu Pro Leu His Pro Ala Ala Met Pro His Leu Leu
1               5                   10                  15

Val Gly Ser Ser Gly Leu Ser Arg Tyr Val Ala Arg Leu Ser Ser Asn
            20                  25                  30

Ser Arg Ile Phe Asn His Gln His Gly Thr Met Gln Asn Leu His Asp
        35                  40                  45

Tyr Cys Ser Arg Asn Leu Tyr Val Ser Leu Leu Leu Tyr Gln Thr
    50                  55                  60

Phe Gly Arg Lys Leu His Leu Tyr Ser His Pro Ile Ile Leu Gly Phe
65                  70                  75                  80

Arg Lys Ile Pro Met Gly Val Gly Leu Ser Pro Phe Leu Leu Ala Gln
                85                  90                  95
```

-continued

```
Phe Thr Ser Ala Ile Cys Ser Val Val Arg Arg Ala Phe Pro His Cys
                100                 105                 110

Leu Ala Phe Ser Tyr Ile Asp Asp Val Val Leu Gly Ala Lys Ser Val
        115                 120                 125

Gln His Leu Glu Ser Leu Phe Thr Ala Val Thr Asn Phe Leu Leu Ser
    130                 135                 140

Leu Gly Val His Leu Asn Pro Asn Lys Thr Lys Arg Trp Gly Tyr Ser
145                 150                 155                 160

Leu Asn Phe Met Gly Tyr Val Ile Gly Cys Tyr Gly Ser Leu Pro Gln
                165                 170                 175

Asp His Ile Ile Gln Lys Ile Lys Glu
                180                 185

<210> SEQ ID NO 13
<211> LENGTH: 185
<212> TYPE: PRT
<213> ORGANISM: Hepatitis B Virus

<400> SEQUENCE: 13

Ala Phe Tyr His Leu Pro Leu His Pro Ala Ala Met Pro His Leu Leu
1               5                   10                  15

Val Gly Ser Ser Gly Leu Ser Arg Tyr Val Ala Arg Leu Ser Ser Asn
                20                  25                  30

Ser Arg Ile Phe Asn His Gln His Gly Thr Met Gln Asn Leu His Asp
            35                  40                  45

Tyr Cys Ser Arg Asn Leu Tyr Val Ser Leu Leu Leu Leu Tyr Gln Thr
    50                  55                  60

Phe Gly Arg Lys Leu His Leu Tyr Ser His Pro Ile Ile Leu Gly Phe
65                  70                  75                  80

Arg Lys Ile Pro Met Gly Val Gly Leu Ser Pro Phe Leu Leu Ala Gln
                85                  90                  95

Phe Thr Ser Ala Ile Cys Ser Val Val Arg Arg Ala Phe Pro His Cys
                100                 105                 110

Leu Ala Phe Ser Tyr Met Asp Asp Val Val Leu Gly Ala Lys Ser Val
        115                 120                 125

Gln His Leu Glu Ser Leu Phe Thr Ala Val Thr Asn Phe Leu Leu Ser
    130                 135                 140

Leu Gly Val His Leu Asn Pro Asn Lys Thr Lys Arg Trp Gly Tyr Ser
145                 150                 155                 160

Leu Asn Phe Met Gly Tyr Val Ile Gly Cys Tyr Gly Ser Leu Pro Gln
                165                 170                 175

Asp His Ile Ile Gln Lys Ile Lys Glu
                180                 185

<210> SEQ ID NO 14
<211> LENGTH: 159
<212> TYPE: PRT
<213> ORGANISM: Hepatitis B Virus
<220> FEATURE:
<221> NAME/KEY: MISC_FEATURE
<222> LOCATION: (5)..(5)
<223> OTHER INFORMATION: X=any
<220> FEATURE:
<221> NAME/KEY: MISC_FEATURE
<222> LOCATION: (153)..(153)
<223> OTHER INFORMATION: X=any
<220> FEATURE:
<221> NAME/KEY: MISC_FEATURE
<222> LOCATION: (156)..(159)
<223> OTHER INFORMATION: X=any
```

<400> SEQUENCE: 14

```
Ile Tyr Ser Leu Xaa Pro Ala Ala Met Pro His Leu Leu Val Gly Ser
1               5                   10                  15

Ser Gly Leu Ser Arg Tyr Val Ala Arg Leu Ser Ser Asn Ser Arg Ile
            20                  25                  30

Phe Asn His Gln His Gly Thr Met Gln Asn Leu His Asp Tyr Cys Ser
        35                  40                  45

Arg Asn Leu Tyr Val Ser Leu Leu Leu Leu Tyr Gln Thr Phe Gly Arg
50                  55                  60

Lys Leu His Leu Tyr Ser His Pro Ile Ile Leu Gly Phe Arg Lys Ile
65                  70                  75                  80

Pro Met Gly Leu Gly Leu Ser Pro Phe Leu Leu Ala Gln Phe Thr Ser
                85                  90                  95

Ala Ile Cys Ser Val Val Arg Arg Ala Phe Pro His Cys Leu Ala Phe
            100                 105                 110

Ser Tyr Ile Asp Asp Val Val Leu Gly Ala Lys Ser Val Gln His Leu
        115                 120                 125

Glu Ser Leu Phe Thr Ala Val Thr Asn Phe Leu Leu Ser Leu Gly Val
    130                 135                 140

His Leu Asn Pro Asn Lys Thr Lys Xaa Trp Gly Xaa Xaa Xaa Xaa
145                 150                 155
```

<210> SEQ ID NO 15
<211> LENGTH: 153
<212> TYPE: PRT
<213> ORGANISM: Hepatitis B Virus
<220> FEATURE:
<221> NAME/KEY: MISC_FEATURE
<222> LOCATION: (5)..(5)
<223> OTHER INFORMATION: X=any
<220> FEATURE:
<221> NAME/KEY: MISC_FEATURE
<222> LOCATION: (153)..(153)
<223> OTHER INFORMATION: X=any

<400> SEQUENCE: 15

```
Ile Tyr Ser Leu Xaa Pro Ala Ala Met Pro His Leu Leu Val Gly Ser
1               5                   10                  15

Ser Gly Leu Ser Arg Tyr Val Ala Arg Leu Ser Ser Asn Ser Arg Ile
            20                  25                  30

Phe Asn His Gln His Gly Thr Met Gln Asn Leu His Asp Tyr Cys Ser
        35                  40                  45

Arg Asn Leu Tyr Val Ser Leu Leu Leu Leu Tyr Gln Thr Phe Gly Arg
50                  55                  60

Lys Leu His Leu Tyr Ser His Pro Ile Ile Leu Gly Phe Arg Lys Ile
65                  70                  75                  80

Pro Met Gly Val Gly Leu Ser Pro Phe Leu Leu Ala Gln Phe Thr Ser
                85                  90                  95

Ala Ile Cys Ser Val Val Arg Arg Ala Phe Pro His Cys Leu Ala Phe
            100                 105                 110

Ser Tyr Ile Asp Asp Val Val Leu Gly Ala Lys Ser Val Gln His Leu
        115                 120                 125

Glu Ser Leu Phe Thr Ala Val Thr Asn Phe Leu Leu Ser Leu Gly Val
    130                 135                 140

His Leu Asn Pro Asn Lys Thr Lys Xaa
145                 150
```

```
<210> SEQ ID NO 16
<211> LENGTH: 70
<212> TYPE: PRT
<213> ORGANISM: Hepatitis B Virus

<400> SEQUENCE: 16

Gly Val Gly Leu Ser Pro Phe Leu Leu Ala Gln Phe Thr Ser Ala Ile
1               5                   10                  15

Cys Ser Val Val Arg Arg Ala Phe Pro His Cys Leu Ala Phe Ser Tyr
            20                  25                  30

Met Asp Asp Val Val Leu Gly Ala Lys Ser Val Gln His Leu Glu Ala
        35                  40                  45

Leu Phe Thr Ala Val Thr Asn Phe Leu Leu Ser Leu Gly Val His Leu
    50                  55                  60

Asn Pro Asn Lys Thr Lys
65                  70

<210> SEQ ID NO 17
<211> LENGTH: 70
<212> TYPE: PRT
<213> ORGANISM: Hepatitis B Virus

<400> SEQUENCE: 17

Gly Val Gly Leu Ser Pro Phe Leu Leu Ala Gln Phe Thr Ser Ala Ile
1               5                   10                  15

Cys Ser Val Val Arg Arg Ala Phe Pro His Cys Leu Ala Phe Ser Tyr
            20                  25                  30

Ile Asp Asp Val Val Leu Gly Ala Lys Ser Val Gln His Leu Glu Ser
        35                  40                  45

Leu Phe Thr Ala Val Thr Asn Phe Leu Leu Ser Leu Gly Val His Leu
    50                  55                  60

Asn Pro Asn Lys Thr Lys
65                  70

<210> SEQ ID NO 18
<211> LENGTH: 70
<212> TYPE: PRT
<213> ORGANISM: Hepatitis B Virus

<400> SEQUENCE: 18

Gly Val Gly Leu Ser Pro Phe Leu Leu Ala Gln Phe Thr Ser Ala Ile
1               5                   10                  15

Cys Ser Val Val Arg Arg Ala Phe Pro His Cys Leu Ala Phe Ser Tyr
            20                  25                  30

Met Asp Asp Val Val Leu Gly Ala Lys Ser Val Gln His Leu Glu Ser
        35                  40                  45

Leu Phe Thr Ala Val Thr Asn Phe Leu Leu Ser Leu Gly Val His Leu
    50                  55                  60

Asn Pro Asn Lys Thr Lys
65                  70

<210> SEQ ID NO 19
<211> LENGTH: 70
<212> TYPE: PRT
<213> ORGANISM: Hepatitis B Virus
```

<400> SEQUENCE: 19

Gly Leu Gly Leu Ser Pro Phe Leu Leu Ala Gln Phe Thr Ser Ala Ile
1               5                   10                  15

Cys Ser Val Val Arg Arg Ala Phe Pro His Cys Leu Ala Phe Ser Tyr
            20                  25                  30

Ile Asp Asp Val Val Leu Gly Ala Lys Ser Val Gln His Leu Glu Ser
        35                  40                  45

Leu Phe Thr Ala Val Thr Asn Phe Leu Leu Ser Leu Gly Val His Leu
    50                  55                  60

Asn Pro Asn Lys Thr Lys
65                  70

<210> SEQ ID NO 20
<211> LENGTH: 70
<212> TYPE: PRT
<213> ORGANISM: Hepatitis B Virus

<400> SEQUENCE: 20

Gly Val Gly Leu Ser Pro Phe Leu Leu Ala Gln Phe Thr Ser Ala Ile
1               5                   10                  15

Cys Ser Val Val Arg Arg Ala Phe Pro His Cys Leu Ala Phe Ser Tyr
            20                  25                  30

Ile Asp Asp Val Val Leu Gly Ala Lys Ser Val Gln His Leu Glu Ser
        35                  40                  45

Leu Phe Thr Ala Val Thr Asn Phe Leu Leu Ser Leu Gly Val His Leu
    50                  55                  60

Asn Pro Asn Lys Thr Lys
65                  70

<210> SEQ ID NO 21
<211> LENGTH: 70
<212> TYPE: PRT
<213> ORGANISM: Hepatitis B Virus

<400> SEQUENCE: 21

Gly Val Gly Leu Ser Pro Phe Leu Leu Ala Gln Phe Thr Ser Ala Ile
1               5                   10                  15

Cys Ser Val Val Arg Arg Ala Phe Pro His Cys Leu Ala Phe Ser Tyr
            20                  25                  30

Met Asp Asp Val Val Leu Gly Ala Lys Ser Val Gln His Leu Glu Ser
        35                  40                  45

Leu Phe Thr Ala Val Thr Asn Phe Leu Leu Ser Leu Gly Ile His Leu
    50                  55                  60

Asn Pro Asn Lys Thr Lys
65                  70

<210> SEQ ID NO 22
<211> LENGTH: 12
<212> TYPE: PRT
<213> ORGANISM: artificial sequence
<220> FEATURE:
<223> OTHER INFORMATION: Tag100 epitope

<400> SEQUENCE: 22

Glu Glu Thr Ala Arg Phe Gln Pro Gly Tyr Arg Ser
1               5                   10

<210> SEQ ID NO 23
<211> LENGTH: 10
<212> TYPE: PRT
<213> ORGANISM: artificial sequence
<220> FEATURE:
<223> OTHER INFORMATION: c-myc epitope

<400> SEQUENCE: 23

Glu Gln Lys Leu Ile Ser Glu Glu Asp Leu
1               5                   10

<210> SEQ ID NO 24
<211> LENGTH: 7
<212> TYPE: PRT
<213> ORGANISM: artificial sequence
<220> FEATURE:
<223> OTHER INFORMATION: FLAG-epitope

<400> SEQUENCE: 24

Asp Tyr Lys Asp Asp Asp Lys
1               5

<210> SEQ ID NO 25
<211> LENGTH: 9
<212> TYPE: PRT
<213> ORGANISM: artificial sequence
<220> FEATURE:
<223> OTHER INFORMATION: HA epitope

<400> SEQUENCE: 25

Tyr Pro Tyr Asp Val Pro Asp Tyr Ala
1               5

<210> SEQ ID NO 26
<211> LENGTH: 12
<212> TYPE: PRT
<213> ORGANISM: artificial sequence
<220> FEATURE:
<223> OTHER INFORMATION: protein C epitope

<400> SEQUENCE: 26

Glu Asp Gln Val Asp Pro Arg Leu Ile Asp Gly Lys
1               5                   10

<210> SEQ ID NO 27
<211> LENGTH: 11
<212> TYPE: PRT
<213> ORGANISM: artificial sequence
<220> FEATURE:
<223> OTHER INFORMATION: VSV epitope

<400> SEQUENCE: 27

Tyr Thr Asp Ile Glu Met Asn Arg Leu Gly Lys
1               5                   10

<210> SEQ ID NO 28
<211> LENGTH: 19
<212> TYPE: DNA
<213> ORGANISM: Hepatitis B Virus

<400> SEQUENCE: 28
ggatgtgtct gcggcgttt                                            19

<210> SEQ ID NO 29
<211> LENGTH: 24
<212> TYPE: DNA
<213> ORGANISM: Hepatitis B Virus -continued

```
<400> SEQUENCE: 29
accccatctt tttgttttgt tagg                                              24

<210> SEQ ID NO 30
<211> LENGTH: 16
<212> TYPE: DNA
<213> ORGANISM: Hepatitis B Virus

<400> SEQUENCE: 30
tggatgtgtc tgcggc                                                       16

<210> SEQ ID NO 31
<211> LENGTH: 25
<212> TYPE: DNA
<213> ORGANISM: Hepatitis B Virus

<400> SEQUENCE: 31
ckttgacada ctttccaatc aatag                                             25

<210> SEQ ID NO 32
<211> LENGTH: 33
<212> TYPE: DNA
<213> ORGANISM: Hepatitis B Virus

<400> SEQUENCE: 32
cttttgtctt tgggtgtaca tttaaaccct aac                                    33

<210> SEQ ID NO 33
<211> LENGTH: 33
<212> TYPE: DNA
<213> ORGANISM: Hepatitis B Virus

<400> SEQUENCE: 33
gttagggttt aaatgtacac ccaaagacaa aag                                    33

<210> SEQ ID NO 34
<211> LENGTH: 24
<212> TYPE: DNA
<213> ORGANISM: Hepatitis B Virus

<400> SEQUENCE: 34
ctccagttca ggaacagtaa accc                                              24

<210> SEQ ID NO 35
<211> LENGTH: 32
<212> TYPE: DNA
<213> ORGANISM: Hepatitis B Virus

<400> SEQUENCE: 35
ttgtgagctc agaaaggcct tgtaagttgg cg                                     32

<210> SEQ ID NO 36
<211> LENGTH: 123
<212> TYPE: PRT
<213> ORGANISM: Hepatitis B Virus

<400> SEQUENCE: 36

Phe Gln Asp Leu Arg Pro Pro Val Arg Asp His Ala Glu Pro Ala Arg
1               5                   10                  15

Leu Leu Leu Lys Glu Pro Leu Cys Ile Pro Pro Val Ala Val Pro Asn
            20                  25                  30
```

-continued

```
Leu Arg Thr Glu Ile Ala Pro Val Phe Pro Ser Ile Ile Leu Gly Phe
        35              40              45

Arg Lys Ile Pro Met Gly Val Gly Leu Ser Pro Phe Leu Leu Ala Gln
    50              55              60

Phe Thr Ser Ala Ile Cys Ser Val Val Arg Arg Ala Phe Pro His Cys
65              70              75              80

Leu Ala Phe Ser Tyr Met Asp Asp Val Val Leu Gly Ala Lys Ser Val
            85              90              95

Gln His Leu Glu Ala Leu Phe Thr Ala Val Thr Asn Phe Leu Leu Ser
            100             105             110

Leu Gly Val His Leu Asn Pro Asn Lys Thr Lys
            115             120
```